United States Patent
Siegel et al.

(10) Patent No.: US 10,682,310 B2
(45) Date of Patent: Jun. 16, 2020

(54) THERAPEUTIC COMPOUNDS AND FORMULATIONS FOR INTRANASAL DELIVERY

(71) Applicant: REGENTS OF THE UNIVERSITY OF MINNESOTA, Minneapolis, MN (US)

(72) Inventors: Ronald A. Siegel, Minneapolis, MN (US); Mamta Kapoor, Minneapolis, MN (US); Narsihmulu Cheryala, Minneapolis, MN (US); Gunda I. Georg, Minneapolis, MN (US); James C. Cloyd, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 95 days.

(21) Appl. No.: 15/559,408

(22) PCT Filed: Mar. 17, 2016

(86) PCT No.: PCT/US2016/022951
§ 371 (c)(1),
(2) Date: Sep. 18, 2017

(87) PCT Pub. No.: WO2016/149540
PCT Pub. Date: Sep. 22, 2016

(65) Prior Publication Data
US 2018/0085306 A1    Mar. 29, 2018

Related U.S. Application Data

(60) Provisional application No. 62/134,903, filed on Mar. 18, 2015.

(51) Int. Cl.
*A61K 38/48*    (2006.01)
*A61K 9/00*    (2006.01)
(Continued)

(52) U.S. Cl.
CPC .............. *A61K 9/0043* (2013.01); *A61K 9/12* (2013.01); *A61K 31/417* (2013.01);
(Continued)

(58) Field of Classification Search
None
See application file for complete search history.

(56) References Cited

U.S. PATENT DOCUMENTS

| RE30,473 E | 1/1981 | Hassall et al. |
| 7,435,422 B2 * | 10/2008 | Warthen .................. A61K 9/19 424/253.1 |
| 2011/0230473 A1 | 9/2011 | Gordon et al. |

FOREIGN PATENT DOCUMENTS

WO    2015017715 A1    2/2015

OTHER PUBLICATIONS

Hou, et al., "Enhanced permeation of diazepam through artificial membranes from supersaturated solutions", Journal of Pharmaceutical Sciences 95(4), 896-905 (2006).
(Continued)

*Primary Examiner* — Renee Claytor
*Assistant Examiner* — Trent R Clarke
(74) *Attorney, Agent, or Firm* — Viksnins Harris Padys Malen LLP

(57) ABSTRACT

Certain embodiments of the invention provide a formulation suitable for nasal administration comprising water, a prodrug of a therapeutic agent, and an enzyme that is suitable for intranasal conversion of the prodrug to the therapeutic agent, as well as methods of use thereof.

2 Claims, 6 Drawing Sheets

(51) Int. Cl.
  A61K 31/5517 (2006.01)
  A61K 9/12 (2006.01)
  A61K 31/417 (2006.01)
  C07D 233/64 (2006.01)
(52) U.S. Cl.
  CPC ........ *A61K 31/5517* (2013.01); *A61K 38/482* (2013.01); *A61K 38/4813* (2013.01); *C07D 233/64* (2013.01); *C12Y 304/11006* (2013.01); *C12Y 304/21063* (2013.01)

(56) References Cited

OTHER PUBLICATIONS

Kapoor, et al., "Chirally Pure Prodrugs and Their Converting Enzymes Lead to High Supersaturation and Rapid Transcellular Permeation of Benzodiazepines", Journal of Pharmaceutical Sciences 105, 2365-2371 (2016).
Kapoor, et al., "Rapid Delivery of Diazepam from Supersaturated Solutions Prepared Using Prodrug/Enzyme Mixtures: Toward Intranasal Treatment of Seizure Emergencies", AAPS J 16(3), 577-585 (2014).
Patent Cooperation Treaty, International Searching Authority, Search Report and Written Opinion for PCT/US2016/22951, 11 pages, Jun. 20, 2016.
Siegel, et al., "Water-soluble benzodiazepine prodrug/enzyme combinations for intranasal rescue therapies", Epilepsy & Behavior 49, 347-350 (2015).
Wermeling, et al., "Intranasal Delivery of Antiepileptic Medications for Treatment of Seizures", Neurotherapeutics: The Journal of the American Society for Experimental Neuro Therapeutics 6, 352-358 (2009).

* cited by examiner

THERAPEUTIC COMPOUNDS AND FORMULATIONS FOR INTRANASAL DELIVERY

PRIORITY OF INVENTION

This application claims priority from U.S. Provisional Patent Application No. 62/134,903 filed Mar. 18, 2015, which is hereby incorporated by reference in its entirety.

BACKGROUND OF THE INVENTION

Currently, there are a number of therapeutic agents for which intranasal delivery would be desirable but which do not have the appropriate solubility. These agents are therefore often delivered intravenously or rectally. However, intravenous administration requires skilled labor and hospitalization, which are time consuming processes that often cause delay in the treatment, while rectal administration often has poor patient compliance. For other agents, intranasal delivery is possible but only when combined with organic excipients, which may cause irritation and slow absorption. Examples of such therapeutic agents include certain benzodiazepines. Currently, intravenous (i.v.) benzodiazepines such as diazepam (DZP), lorazepam, or midazolam (MDZ) are the first choice drugs for the treatment of status epilepticus (SE), acute repetitive seizures (ARS) and other neurological emergencies. Rectal DZP is effective for ARS, but both patients and caregivers object to this route of administration, resulting in poor patient compliance. Soon to be marketed intranasal formulations also exist, but these formulations are based on organic excipients.

Thus, there is a need for new intranasal formulations of therapeutic agents, e.g., new formulations of benzodiazepines, as well as new compounds and formulations for the treatment of diseases or disorders, such as SE.

SUMMARY OF THE INVENTION

Accordingly, as described herein, certain embodiments of the present invention provide intranasal formulations based on water soluble prodrug/enzyme combinations, which can be rendered in an aqueous form. Intranasal aqueous delivery systems possess distinct advantages over i.v. and rectal delivery, as well as over intranasal systems that include organic excipients, including simplified administration, improved patient compliance and/or reduced irritation. Moreover, the prodrug and enzyme combination described herein may also produce supersaturated drug solutions that will be more rapidly absorbed across the nasal mucosal membranes than a drug that is solubilized by organic excipients.

Thus, certain embodiments of the invention provide a formulation suitable for nasal administration comprising water, a prodrug of a therapeutic agent, or a salt thereof, and an enzyme that is suitable for intranasal conversion of the prodrug to the therapeutic agent.

Certain embodiments of the invention provide a kit comprising a) a prodrug in an aqueous solution; b) an enzyme; and c) instructions for concurrent intranasal administration of the prodrug and enzyme. In certain embodiments, the prodrug and enzyme are in separate containers. In certain embodiments, the prodrug and enzyme are in a single container, wherein the prodrug and enzyme are in separate compartments within the container.

Certain embodiments of the invention provide a method of delivering a therapeutic agent to an animal (e.g., a mammal, e.g., a human), comprising intranasally administering to the animal a formulation described herein.

Certain embodiments of the invention provide a method for treating or preventing a disease or disorder (e.g., a neurological disorder) in an animal comprising administering a formulation described herein to the animal intranasally.

The invention also provides a formulation described herein for use in medical therapy.

The invention also provides a formulation described herein for the prophylactic or therapeutic treatment of a disease or disorder.

The invention also provides the use of a formulation described herein to prepare a medicament for treating a disease or disorder in an animal.

Certain embodiments of the invention provide the following compound:

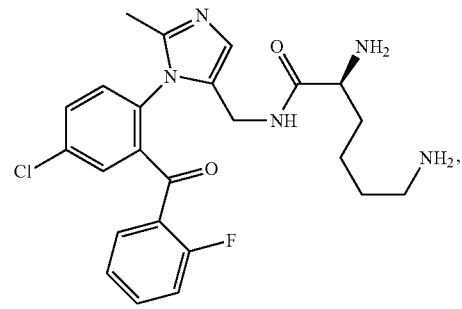 [SMILES: Cc1ncc(CNC(=O)[C@@H](N)CCCCN)n1-c1ccc(Cl)cc1C(=O)c1ccccc1F]

or a salt thereof.

Certain embodiments of the invention also provide a method for preparing a protected lysine prodrug of a therapeutic agent having an amino group, comprising reacting the amino group of the ring-opened therapeutic agent with:

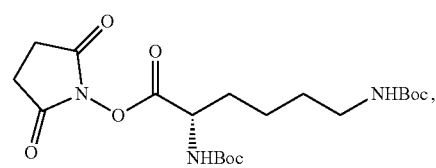

to provide the protected lysine prodrug of the therapeutic agent.

The invention also provides processes and intermediates disclosed herein that are useful for preparing prodrugs of therapeutic compounds or salts thereof.

Figure 1:
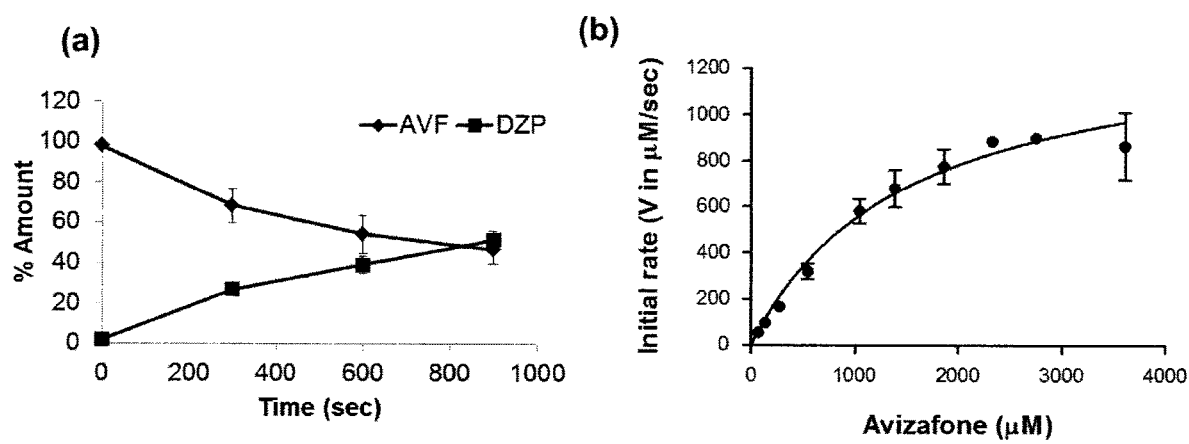
FIG. 1. (a) Reaction kinetics of avizafone-*Aspergillus orizae* (AVF-A.O.) protease mixture prepared using 0.25 U/mL A.O. protease and 1041.6 μM AVF at 32° C. in a shaker. (b) Prodrug conversion rate (at 5 min) as a function of its concentration using 0.25 U/mL A.O. protease. Symbols represent the experimental data and the regression line is data fitted to the Michaelis-Menten equation. Mean±SD, n=3.

$$c_d^b(t) = \frac{V_a C_d^0}{V_a + V_b}\left[1 - e^{-(CL_d/V_{a|b})t}\right],$$

permitting determination of clearance, CL. In this equation, $$\frac{1}{V_{a|b}} = \frac{1}{V_a} + \frac{1}{V_b},$$

where $V_a$ and $V_b$ are the volumes of the apical and basal compartments, respectively. (b) MDZ-pro and MDZ kinetics in the apical chamber following administration of MDZ-pro (S=6)/A.O. protease (16 U/mL). Dashed line is the prediction of a two compartment model using the following equation:

$$c_d^a(t) = \frac{V_a C_p^0}{V_a + V_b}\left[1 - e^{-k_{com}t} + \frac{V_b}{V_a}k_{conv}\frac{e^{-k_{com}t} - e^{-(CL_d/V_{a|b})t}}{(CL_d/V_{a|b}) - k_{conv}}\right],$$

with CL as determined in (a) and conversion rate constant $k_{conv}$, given by $V_{max}/K_M$. Note that MDZ levels are far above solubility (55 μM). (c) Accumulation of MDZ in the basal compartment following administration of MDZ-pro/A.O. protease (16 U/mL), at various MDZ-pro supersaturation potentials (S) into the apical compartment. Curves are predictions based on the following equation:

$$c_d^b(t) = \frac{Dose_p}{V_a + V_b}\left[1 - e^{-k_{com}t} - k_{conv}\frac{e^{-k_{conv}t} - e^{-(CL_d/V_{a|b})t}}{(CL_d/V_{a|b}) - k_{conv}}\right]$$

based on the two compartment model. (d) Early time MDZ flux at different S values obtained from data (symbols) in (c), taken at 5, 10, and 15 min. Line is regression fit through origin. All experiments were performed in assay buffer, pH 7.4 at 32° C. using 12-well Transwell plates. Mean±SD. n=4.

DETAILED DESCRIPTION

As described herein, certain embodiments of the invention provide a formulation suitable for nasal administration comprising water, a prodrug of a therapeutic agent, or a salt thereof, and an enzyme that is suitable for intranasal conversion of the prodrug to the therapeutic agent.

As used herein, the term "therapeutic agent" includes active therapeutic compounds as well as corresponding precursors for active therapeutic compounds "precursors of therapeutic compounds" that are capable of being converted (e.g. cyclizing) to provide the active therapeutic compounds. For example, in relation to the active therapeutic compound midazolam (10), the term "therapeutic agent" includes the ring-opened precursor 101 that can cyclize to provide the active therapeutic compound midazolam.

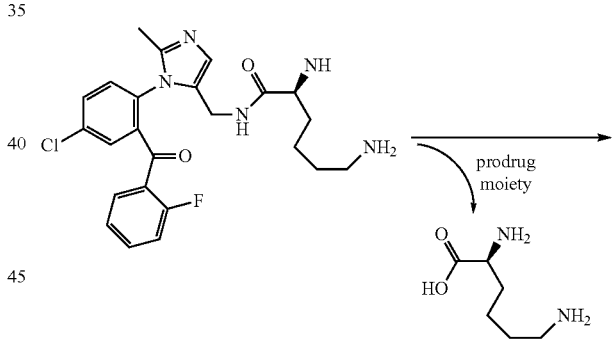

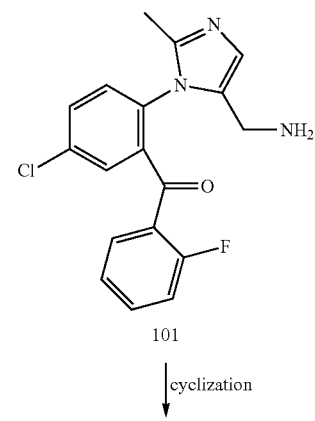

101

↓ cyclization

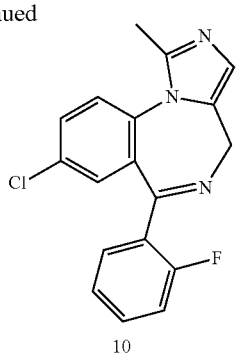

10

In one embodiment, the invention provides a formulation suitable for nasal administration comprising: water, a prodrug of a therapeutic agent, and an enzyme that is suitable for intranasal conversion of the prodrug to the therapeutic agent, wherein the therapeutic agent is midazolam or a precursor of midazolam. It should be understood that the term "precursor of midazolam" includes compounds that are capable of being converted (e.g. cyclizing) to provide midazolam once a prodrug moiety has been removed from the prodrug. In one embodiment, a "precursor of a therapeutic compound" is converted to the corresponding active therapeutic compound in vivo. In one embodiment, a "precursor of a therapeutic compound" is converted to the corresponding active therapeutic compound in one step following removal of a prodrug moiety. In one embodiment, a "precursor of a therapeutic compound" is converted to the corresponding active therapeutic compound spontaneously following removal of a prodrug moiety. In one embodiment, a "precursor of a therapeutic compound" is converted to the corresponding active therapeutic compound by intramolecular cyclization following removal of a prodrug moiety. In one embodiment the therapeutic agent is an active therapeutic compound. In one embodiment the therapeutic agent is a precursor of a therapeutic compound.

In certain embodiments, the formulation comprises at least about 2%, 5%, 10%, 15%, 20%, 25%, 30%, 35%, 40%, 45%, 50%, 55%, 60%, 70%, 80%, 90%, 95%, or 99% water by weight.

In certain embodiments, the formulation further comprises one or more water soluble excipients (e.g., salts, sugars, or water soluble polymers).

In certain embodiments, the formulation is significantly free of surfactants or organic solubilizing agents, such as cyclodextrins, cremophor, propylene glycol, or glycofurol. In certain embodiments, this term indicates the formulation comprises less than about 10%, 9%, 8%, 7%, 6%, 5%, 4%, 3%, 2%, 1%, 0.5%, 0.1% by weight of surfactants or organic solubilizing agents.

Therapeutic Agents

Therapeutic agents are agents that provide a therapeutically desirable effect when administered to an animal (e.g., a mammal, such as a human). As used herein, the therapeutic agent may be any therapeutic agent for which rapid delivery and/or absorption is desired (e.g., rapid absorption across nasal membranes). Therapeutic agents are known in the art and lists of agents can be found, for example, in: Physicians' Desk Reference, 55 ed., 2001, Medical Economics Company, Inc., Montvale, N.J.; USPN Dictionary of USAN and International Drug Names, 2000, The United States Pharmacopeial Convention, Inc., Rockville, Md.; and The Merck Index, 12 ed., 1996, Merck & Co., Inc., Whitehouse Station, N.J.

Typically, the therapeutic agent will contain a functional group, which will allow it to be converted to a prodrug either directly or through a removable linking group. Suitable functional groups include alcohols, amines, esters and amides.

In certain embodiments, the therapeutic agent has low aqueous solubility. In certain embodiments, aqueous formulations of the therapeutic agent are not possible due to low solubility of the agent. As described herein, these agents may be converted into an aqueous soluble prodrug, which allows for the preparation of a formulation suitable for nasal administration as described herein.

In certain embodiments, the therapeutic agent has a molecular mass of less than or about 1500 g mol$^{-1}$. In certain embodiments, the therapeutic agent has a molecular mass less than or about 1000 g mol$^{-1}$. In certain embodiments, the therapeutic agent has a molecular mass less than or about 750 g mol$^{-1}$. In certain embodiments, the therapeutic agent has a molecular mass less than or about 500 g mol$^{-1}$. In certain embodiments, the therapeutic agent has a molecular mass less than or about 400 g mol$^{-1}$. In certain embodiments, the therapeutic agent has a molecular mass less than or about 300 g mol$^{-1}$. In certain embodiments, the therapeutic agent has a molecular mass less than or about 250 g mol$^{-1}$. In certain embodiments, the therapeutic agent has a molecular mass less than or about 200 g mol$^{-1}$. In certain embodiments, the therapeutic agent has a molecular mass less than or about 150 g mol$^{-1}$. In certain embodiments, the therapeutic agent has a molecular mass less than or about 100 g mol$^{-1}$.

In certain embodiments, the therapeutic agent is an anti-seizure agent.

In certain embodiments, the therapeutic agent is a benzodiazepine. In certain embodiments, the benzodiazepine is selected from lorazepam, diazepam (DZP), quazepam, estazolam, clobazam, flurazepam, alprazolam, oxazepam, chlordiazepoxide, clonazepam, clorazepate, midazolam, triazolam, temazepam and halazepam.

In certain embodiments, the therapeutic agent is diazepam (DZP).

In certain embodiments, the therapeutic agent is midazolam (MDZ).

In certain embodiments, the therapeutic agent is lorazepam.

Prodrug Moieties

As described herein, a prodrug moiety is a group that may be linked to a therapeutic agent (e.g. a therapeutic compound or a precursor of a therapeutic compound) to increase the water solubility of the therapeutic agent. Thus, a prodrug as used herein is a compound wherein a prodrug moiety is linked to a therapeutic agent (e.g. a therapeutic compound or a precursor of a therapeutic compound).

In certain embodiments, the prodrug moiety is an acid that contains an ionizable group(s), for example, an amino acid such as lysine, arginine, histidine, aspartic acid or glutamic acid. In other embodiments, the prodrug moiety is a non-proteinogenic amino acid, a dicarboxylic acid, or a phosphate.

In certain embodiments, the prodrug moiety is a lysine moiety (e.g., an L-lysine moiety).

Embodiments of Certain Prodrugs

In certain embodiments, the prodrug is the following compound or a salt thereof:

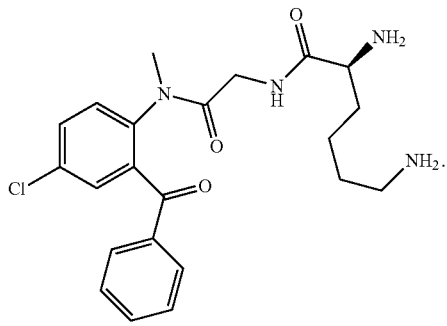 [SMILES: CN(C(=O)CNC(=O)[C@@H](N)CCCCN)c1ccc(Cl)cc1C(=O)c1ccccc1]

In certain embodiments, the prodrug is a salt.
In certain embodiments, the prodrug is the following salt:

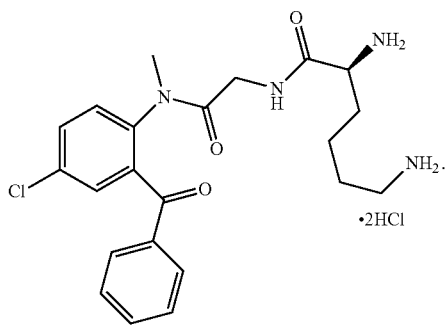 [SMILES: CN(C(=O)CNC(=O)[C@@H](N)CCCCN)c1ccc(Cl)cc1C(=O)c1ccccc1]

In certain embodiments, the prodrug is the following compound

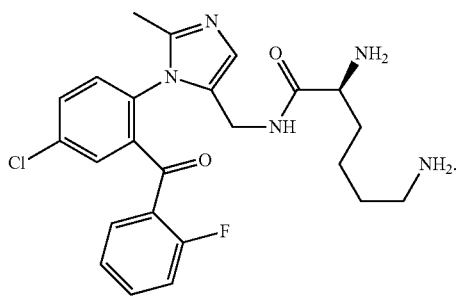 [SMILES: Cc1ncc(CNC(=O)[C@@H](N)CCCCN)n1-c1ccc(Cl)cc1C(=O)c1ccccc1F]

or a salt thereof.
In certain embodiments, the prodrug is a salt.
In certain embodiments, the prodrug is the following salt:

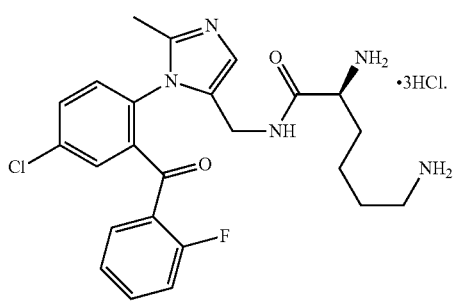 [SMILES: Cc1ncc(CNC(=O)[C@@H](N)CCCCN)n1-c1ccc(Cl)cc1C(=O)c1ccccc1F]

Enzymes

Enzymes are biological molecules that catalyze chemical reactions. As described herein, an enzyme may be any enzyme capable of converting the prodrug of a therapeutic agent into the corresponding therapeutic agent intranasally. In certain embodiments, the enzyme converts the prodrug intranasally into a supersaturated aqueous form of the therapeutic agent, wherein the agent is capable of rapidly crossing mucosal membranes.

In certain embodiments, the enzyme is selected from an esterase, an amidase, a protease, a proteinase, a phosphatase, and an aminopeptidase.

In certain embodiments, the enzyme is a protease.

In certain embodiments, the enzyme is a fungal protease.

In certain embodiments, the enzyme is a fungal protease from *Aspergillus orizae* (O.A). In certain embodiments, the enzyme is EC 3.4.21.63 (Sigma Chemical).

In certain embodiments, the enzyme is a human aminopeptidase. In certain embodiments, the enzyme is EC 3.4.11.6 (Aminopeptidase B).

In certain embodiments, the enzyme is capable of converting Avizafone (AVF) to diazepam (DZP) intranasally, i.e., by cleaving the lysine prodrug moiety from the ring-opened diazepam.

In certain embodiments, the enzyme is capable of converting the midazolam-lysine prodrug described herein (MDZ-pro) to midazolam (MDZ) intranasally, i.e., by cleaving the lysine prodrug moiety from the ring-opened midazolam.

Prodrug and Enzyme Concentrations and Ratios

In certain embodiments, a formulation described herein comprises, e.g., at least about 10 µM, 100 µM, 500 µM, 1 mM, 5 mM, 10 mM, 50 mM, 100 mM, 200 mM, 300 mM, 400 mM, 500 mM, or more of the prodrug. In certain embodiments, a formulation described herein comprises, e.g., less than about 10 M, 5 M, 1 M, 0.5 M, 0.1 M or less of the prodrug. In certain embodiments, a formulation described herein comprises between about 10 µM to about 10 M of the prodrug, between about 1 mM to about 1 M of the prodrug or between about 1 mM to about 500 mM of the prodrug.

In certain embodiments, a formulation described herein comprises, e.g., at least about 0.1 U/ml, 0.25 U/ml, 0.50 U/ml, 1.0 U/ml, 5.0 U/ml, 10.0 U/ml, 50 U/ml, 100 U/ml or more of the enzyme. In certain embodiments, a formulation described herein comprises, e.g., less than about 200 U/ml, 100 U/ml, 50 U/ml, 10.0 U/ml, 5.0 U/ml or less of the enzyme. In certain embodiments, a formulation described herein comprises between about 0.1 U/ml to about 100 U/ml of the enzyme. In certain embodiments, a formulation described herein comprises between about 0.1 U/ml to about 50 U/mol of the enzyme. In certain embodiments, a formulation described herein comprises between about 5 U/ml to about 15 U/ml of the enzyme. In certain embodiments, the formulation comprises about 0.25 U/ml of the enzyme.

In certain embodiments, the ratio of the prodrug to the enzyme ranges between about 25 µM prodrug/0.25 U/ml enzyme to about 20,000 µM prodrug/0.25 U/ml enzyme. In certain embodiments, the ratio of the prodrug to the enzyme ranges between about 25 µM prodrug/0.25 U/ml enzyme to about 5,000 µM prodrug/0.25 U/ml enzyme. In certain embodiments, the ratio of the prodrug to the enzyme ranges between about 50 µM prodrug/0.25 U/ml enzyme to about 5,000 µM prodrug/0.25 U/ml enzyme. In certain embodiments, the ratio of the prodrug to the enzyme ranges between about 25 µM prodrug/0.25 U/ml enzyme to about 2,500 µM prodrug/0.25 U/ml enzyme.

Diseases or Disorders

Certain embodiments of the invention provide a method for treating or preventing a disease or disorder in an animal comprising administering a formulation described herein to the animal intranasally.

The term "treatment" or "treating," to the extent it relates to a disease or disorder includes inhibiting the disease or disorder and/or eliminating the disease or disorder and/or relieving one or more symptoms of the disease or disorder. The term "preventing" or "prevention" includes preventing the disease or disorder from occurring or lessening the severity of the disease or disorder.

In certain embodiments, the disease or disorder is a neurological disorder, such as seizure disorders, migraines, anxiety disorders, impulse control disorders or other types of neurological emergencies. Accordingly, in certain embodiments, the neurological disorder is a seizure disorder, migraines, an anxiety disorder, an impulse control disorder or another type of neurological emergency.

As used herein, seizure disorders may include, but are not limited to, e.g., an epileptic seizure(s), status epilepticus, cluster or acute repetitive seizures, or refractory epilepsy. For example, certain embodiments of the invention provide a method for treating status epilepticus or cluster or acute repetitive seizures in an animal comprising administering a formulation described herein to the animal intranasally. Certain other embodiments of the invention provide a method for preventing seizures in an animal with refractory epilepsy comprising administering a formulation described herein to the animal intranasally.

As used herein anxiety disorders may include, but are not limited to, e.g., panic disorders (e.g., panic attacks), social anxiety disorders, specific phobias and generalized anxiety disorders. Individuals suffering from panic disorders often have feelings of terror that strike suddenly and repeatedly with no warning. Other symptoms of this disorder may also include sweating, chest pain, palpitations (unusually strong or irregular heartbeats), and a feeling of choking, which may make the person feel like he or she is having a heart attack. Social anxiety disorder, also referred to as a social anxiety disorder, often involves overwhelming worry and self-consciousness about everyday social situations; this worry often centers on a fear of being judged by others, or behaving in a way that might cause embarrassment or lead to ridicule. A specific phobia is characterized by an intense fear of a specific object or situation, such as snakes, heights, or flying. The level of fear is usually inappropriate to the situation and may cause the person to avoid common, everyday situations. A generalized anxiety disorder is typically characterized by excessive, unrealistic worry and tension, even if there is little or nothing to provoke the anxiety. Accordingly, certain embodiments of the invention provide a method for treating an anxiety disorder in an animal comprising administering a formulation described herein to the animal intranasally.

As used herein impulse control disorders may include, but are not limited to, e.g., addiction, such as a gambling addiction. Accordingly, certain embodiments of the invention provide a method for treating or preventing episodes of an impulse control disorder in an animal comprising administering a formulation described herein to the animal intranasally.

Midazolam L-Lysine Prodrug

Certain embodiments of the invention provide the following compound:

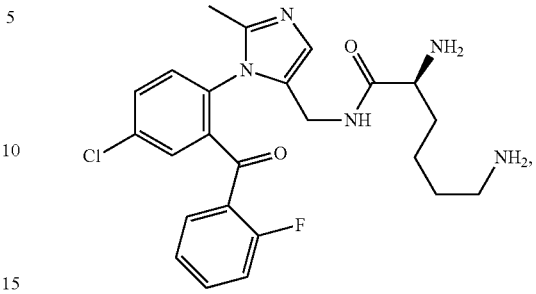

or a salt thereof.

Certain embodiments of the invention provide a salt of the following compound:

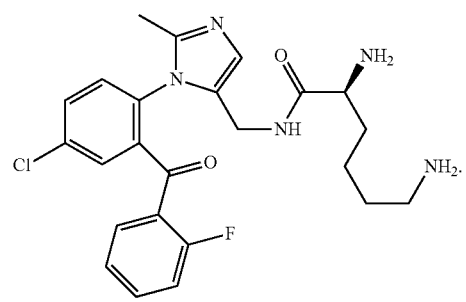 [SMILES: Cc1ncc(CNC(=O)[C@@H](N)CCCCN)n1-c1ccc(Cl)cc1C(=O)c1ccccc1F]

In certain embodiments, the salt is:

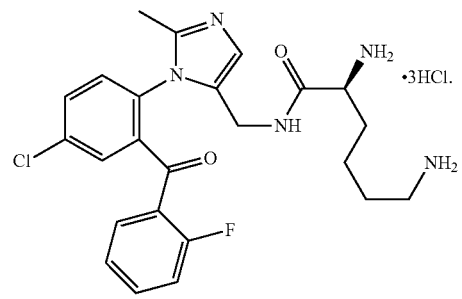 [SMILES: Cc1ncc(CNC(=O)[C@@H](N)CCCCN)n1-c1ccc(Cl)cc1C(=O)c1ccccc1F]

The invention also provides a pharmaceutical composition comprising compound:

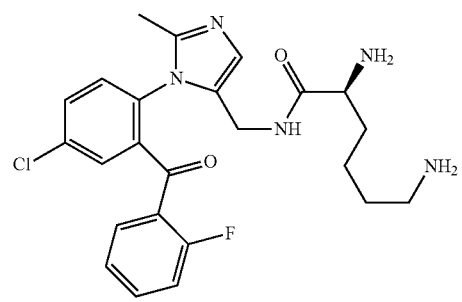 [SMILES: Cc1ncc(CNC(=O)[C@@H](N)CCCCN)n1-c1ccc(Cl)cc1C(=O)c1ccccc1F]

or a pharmaceutically acceptable salt thereof, and a pharmaceutically acceptable excipient.

Certain embodiments of the invention provide a method of treating or preventing a disease or disorder in an animal comprising administering a compound:

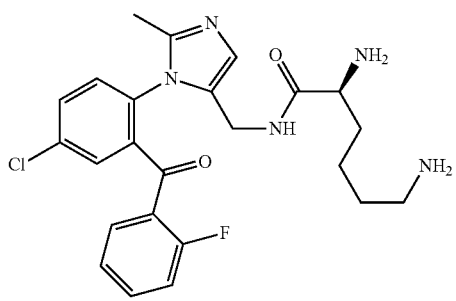 [SMILES: Cc1ncc(CNC(=O)[C@@H](N)CCCCN)n1-c1ccc(Cl)cc1C(=O)c1ccccc1F]

or a pharmaceutically acceptable salt thereof, to the animal.

In certain embodiments, the compound is administered to the animal orally, rectally or intravenously. In certain embodiments, the compound is administered to the animal by injection.

Certain embodiments of the invention provide a compound:

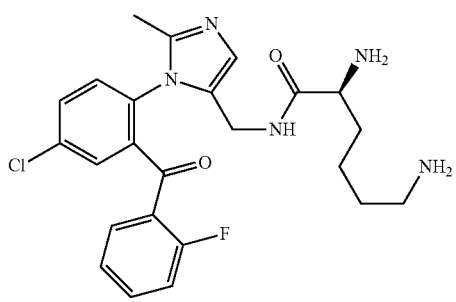

or a pharmaceutically acceptable salt thereof, for use in medical therapy.

Certain embodiments of the invention provide a compound:

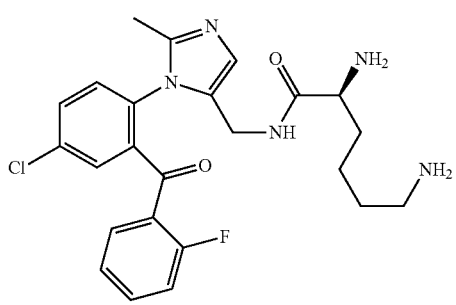 [SMILES: Cc1ncc(CNC(=O)[C@@H](N)CCCCN)n1-c1ccc(Cl)cc1C(=O)c1ccccc1F]

or a pharmaceutically acceptable salt thereof, for the prophylactic or therapeutic treatment of a disease or disorder.

Certain embodiments of the invention provide a compound:

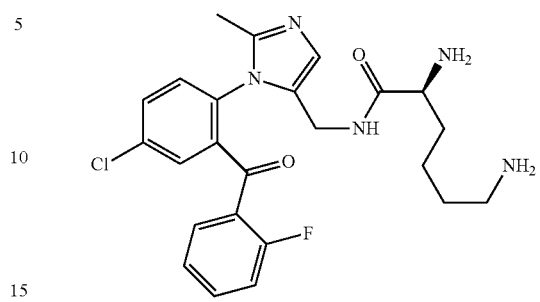

or a pharmaceutically acceptable salt thereof, to prepare a medicament for treating a disease or disorder in an animal.

In certain embodiments, the pharmaceutically acceptable salt is:

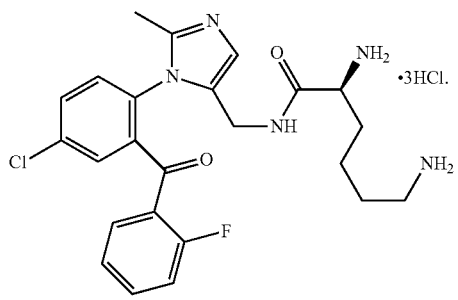 [SMILES: Cc1ncc(CNC(=O)[C@@H](N)CCCCN)n1-c1ccc(Cl)cc1C(=O)c1ccccc1F]

Methods and Intermediates for Preparing a Lysine Prodrug

As described herein, it has been determined that the following compound:

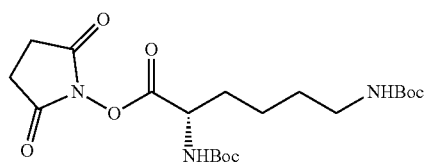

is generally useful for preparing lysine prodrugs of therapeutic agents having an amino group. The advantage of the Boc protected compound 6 is that the prodrug can be formed and deprotected without racemization of the chiral lysine center. Accordingly, certain embodiments of the invention provide a method for preparing a protected lysine prodrug of a therapeutic agent having an amino group, comprising reacting the amino group of the therapeutic agent with:

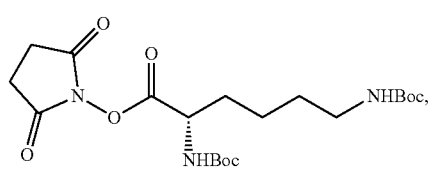

to provide the protected lysine prodrug of the therapeutic agent. The protected lysine prodrug is an intermediate useful for preparing a prodrug described herein. Specifically, the protected lysine prodrug may be converted into a prodrug by removing the Boc protection group (e.g., with an acid).

Certain embodiments of the invention provide compound 7:

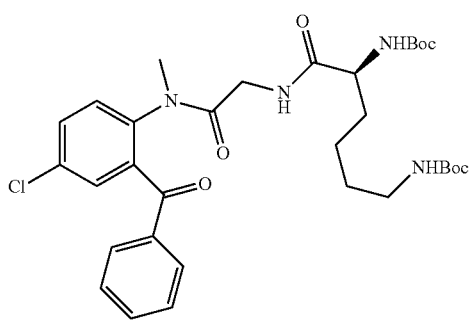

7 or a salt thereof.

Certain embodiments of the invention provide a method of preparing compound 9

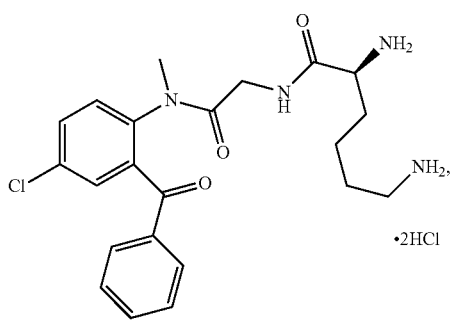

9

·2HCl comprising converting compound 7:

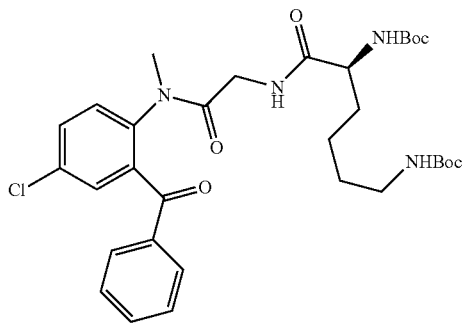

7 to compound 9. In certain embodiments, compound 7 is converted to compound 9 with an acid. In certain embodiments, the acid is HCl. In certain embodiments, the conversion is carried out in a suitable solvent (e.g., a solvent comprising dioxane).

Certain embodiments of the invention provide a method of preparing compound 7:

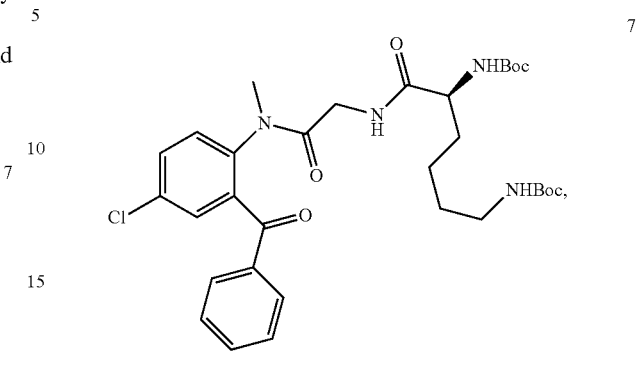

7 comprising converting compound 5:

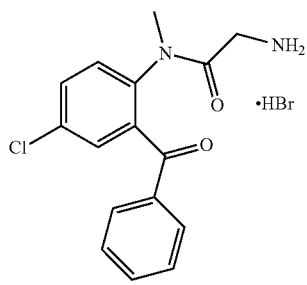

5

·HBr to compound 7 In certain embodiments, compound 5 is converted to compound 7 with compound 6:

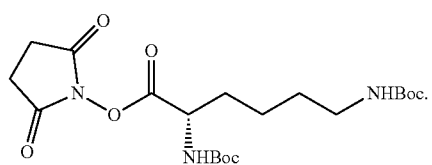

6

Certain embodiments of the invention provide compound 12:

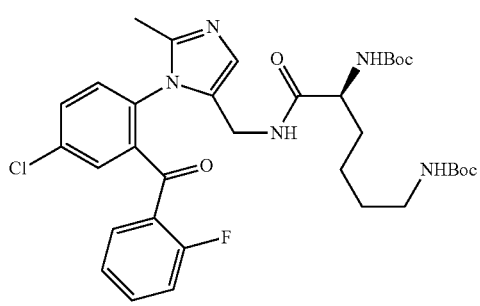

12 or a salt thereof.

Certain embodiments of the invention provide a method of preparing compound 13:

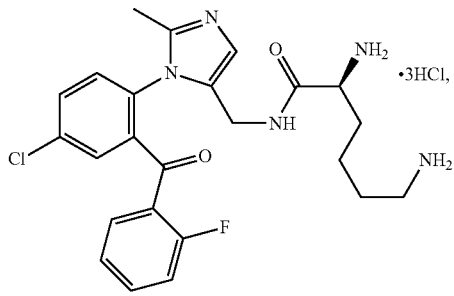 [SMILES: Cc1ncc(CNC(=O)[C@@H](N)CCCCN)n1-c1ccc(Cl)cc1C(=O)c1ccccc1F]

comprising converting compound 12:

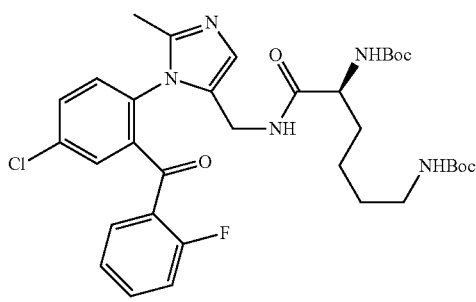

to compound 13. In certain embodiments, compound 12 is converted to compound 13 with an acid. In certain embodiments, the acid is HCl. In certain embodiments, the conversion is carried out in a suitable solvent (e.g., a solvent comprising dioxane).

Certain embodiments of the invention provide a method of preparing compound 12:

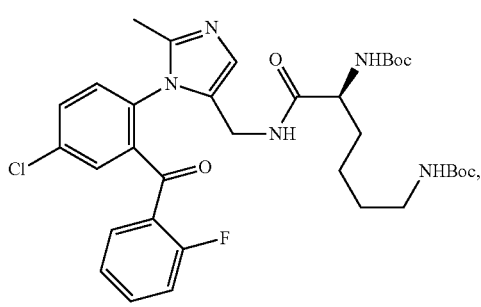

comprising converting compound 11:

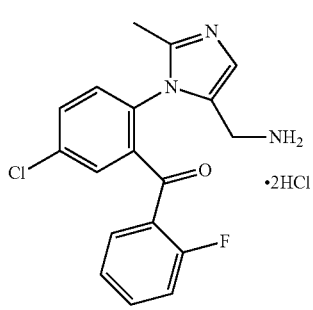

to compound 12. In certain embodiments, compound 11 is converted to compound 12 with compound 6:

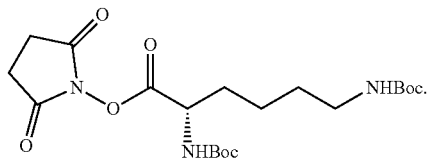

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

In cases where compounds are sufficiently basic or acidic, a salt of a compound described herein can be useful as an intermediate for isolating or purifying the compound. Additionally, administration of a compound described herein as a pharmaceutically acceptable acid or base salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

As described herein, formulations of the invention may be administered intranasally to a mammalian host, such as a human. For example, effective amounts of the formulations described herein may be administered intranasally by spraying the formulation into a nasal cavity or nostril of the subject. In some embodiments, the formulation is within a non-pressurized dispenser. Suitable dispensers include, but are not limited to, a spray pump and a bottle. Various spray volumes can be used to practice the method. In some embodiments, the spray volume ranges from about 10 µL to about 200 µL per nasal cavity or nostril. In some embodiments, the spray volume ranges from about 20 µL, to about 50 µL per nasal cavity or nostril. In some embodiments, the spray volume ranges from about 50 µL, to about 100 µL per nasal cavity or nostril.

In certain embodiments, the prodrug and enzyme are in separate compartments in a container, e.g., a dispenser. The prodrug and enzyme components are then mixed in the applicator just prior to intranasal instillation (e.g., by making use of a mechanism that rapidly dissolves the prodrug and/or enzyme in a carrier buffer), thereby generating a formulation described herein.

In certain embodiments, such formulations typically will contain, e.g., at least about 10 µm of the prodrug. In certain embodiments, such formulations typically will also contain, e.g., at least about 0.1 U/ml of the enzyme. However, the prodrug and enzyme amounts in such therapeutically useful formulations are such that an effective dosage level of the therapeutic agent will be obtained. The ultimate concentrations of the prodrug and enzyme may be determined by one skilled in the art and will vary based on a number of factors, including but not limited to, e.g., the particular prodrug and enzyme combination selected and the activity and turnover rate of the enzyme.

The formulations described herein may further comprise one or more suitable carriers and/or excipients, including but not limited to, pH buffers, osmolytes (e.g. salts, dextrose) and/or thickeners (e.g. polyvinylpyrrolidone).

Generally, useful dosages of the present formulations can be determined by comparing their in vitro activity, and in vivo activity in animal models. Methods for the extrapolation of effective dosages in mice, and other animals, to humans are known to the art; for example, see U.S. Pat. No. 4,938,949.

The amount of the formulation required for use in treatment will vary not only with the particular prodrug/enzyme combination selected, but also with the route of administration, the nature of the condition being treated and the age and condition of the patient, and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple sprays from a dispenser.

Additionally, the compounds described herein (e.g., the midazolam L-lysine prodrug described herein), or salts thereof, may be formulated as pharmaceutical compositions and administered to a mammalian host, such as a human patient in a variety of forms adapted to the chosen route of administration, i.e., orally, rectally or parenterally, by intravenous, intramuscular, topical, intranasal or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. Proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients, enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the present compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the present compounds can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Example.

EXAMPLE 1

Avizafone (AVF) is a prodrug of diazepam (DZP) that has been used in Europe for the intramuscular treatment of seizures induced by organophosphorous nerve agents. When administered systemically, it is converted to DZP by endogenous enzymes. However, the precise activating (converting) enzyme for AVF is unknown. As described herein, a prodrug-enzyme based system for intranasal delivery has been developed for DZP (Diazepam) using AVF (Avizafone) as the prodrug and for a midazolam-lysine prodrug (MDZ-pro). Specifically, screening studies were performed to identify an activating enzyme. A fungal protease from *Aspergillus orizae* (A.O.) was identified by measuring change in ultraviolet (UV) absorbance at 240 nm in a cuvette as a function of time. Since the absorbance of DZP is greater than that of AVF, conversion of AVF to DZP resulted in a steady increase in absorbance over ten minutes in the presence of A.O. protease, but not in the presence of other tested enzymes or in enzyme free media. Similarly, A.O. protease uniquely catalyzed the conversion of MDZ-pro to MDZ. Further, additional studies were carried out using HPLC as a means to separate prodrug from active drug, which enabled determination of the enzyme kinetics (Michaelis-Menten) parameters for each reaction. Reaction kinetic studies for AVF to DZP are summarized in FIG. 1.

In vitro permeation studies were also performed on prodrug/enzyme mixtures prepared at various prodrug and enzyme concentrations. It was subsequently shown that enzymatic conversion of AVF to DZP creates a supersaturated aqueous form of DZP, which rapidly crosses mucosal membranes. The same was also shown for MDZ-pro. The experiments were carried out as follows. Maden Darby Canine Kidney-II wild type (MDCK-IIwt) cells were plated on thin membranes in a six well Transwell apparatus. Following confluence and washing, assay buffer (PBS, pH 7.4) was introduced into the basal side of the membrane. At time zero, solutions of various concentrations of prodrug were combined with 0.25 U/ml of A.O protease and introduced on the basal side of the membrane. Aliquots were then taken, with replacement, from both the basal and apical sides, and assayed for both drug and prodrug. The integrity of the membranes throughout the experiment was confirmed by transepithelial resistance (TEER) and inulin permeation measurements.

An important parameter in the experiments was the supersaturation potential, defined as $$S = \frac{\text{Molar concentration of prodrug}}{\text{Molar concentration of saturated active drug}}$$

This parameter is the degree of supersaturation that the drug solution would achieve if all prodrug was immediately converted to active drug. Values of S greater than unity signify the possibility that the active drug will appear at higher than saturated concentrations following enzymatic conversion of the prodrug.

Figure 2:
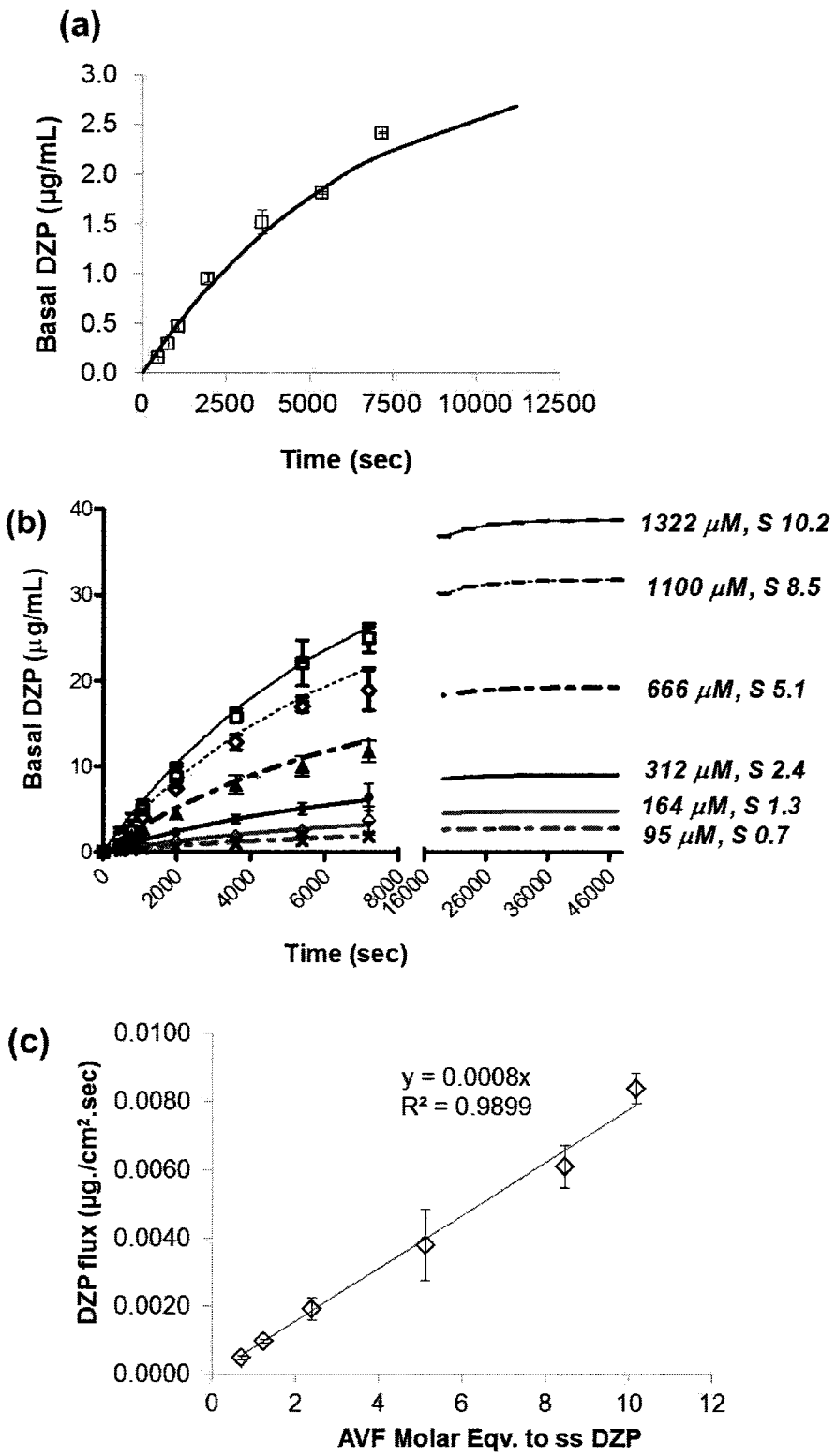
FIG. 2. (a) Permeability of DZP across MDCKII-wt monolayer at near saturation solubility (85.7 μM, S=0.7) (symbols) with flux 0.00045±0.00007 μg/cm$^2$·sec. (b) Accumulation rate (on the basal side of monolayer) of DZP (symbols) produced from AVF-A.O. protease mixtures prepared with different initial prodrug concentrations (μM). 'S' represents the AVF molar equivalent of supersaturated (ss) DZP. (c) DZP flux at different 'S' values obtained from data (symbols) in (b). (d) Concentration-time profile for the AVF-A.O. protease reaction (AVF at S=5.6, $c_{enz}$=4 U/mL) on the apical side of MDCKII-wt membrane. 'Total' amount includes the amount permeating into the basal side. (e) % of DZP produced from prodrug-enzyme mixture (AVF at S=5.6, $c_{enz}$=4 U/mL) in apical compartment (symbols) compared to predicted values (solid line). (f) Concentration-time profile for DZP produced as a result of prodrug/enzyme mixture introduced onto the apical side prepared at various prodrug/enzyme ratios. In parts (d)-(f), the horizontal line represents DZP saturation level (S=1, $c_{d,sat}$). These experiments were performed in assay buffer, pH 7.4 at 32° C. using 12-well Transwell plates. Mean±SD, n=4.
Figure 2:
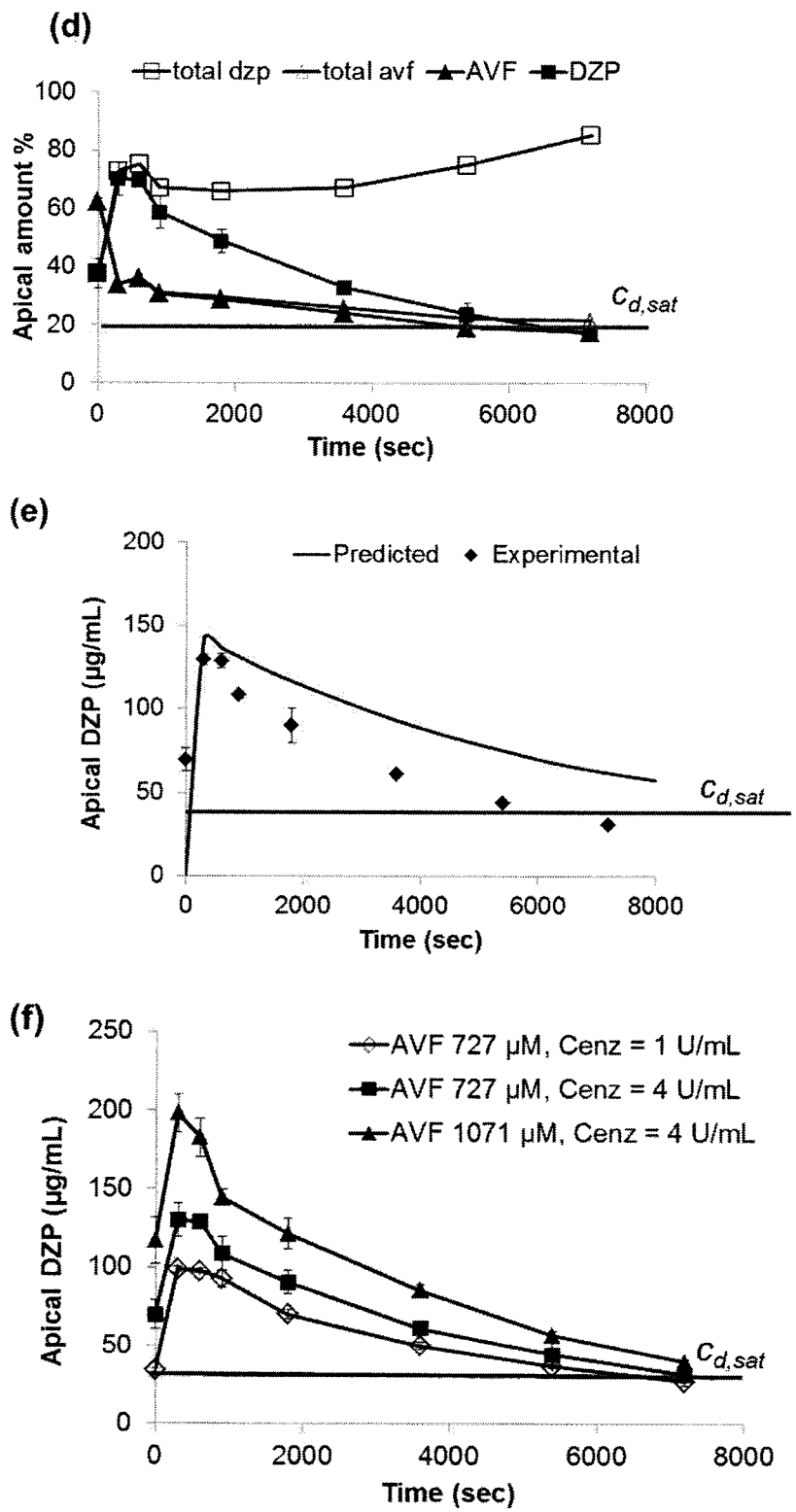

FIG. 2 summarizes experiments monitoring the conversion of AVF to DZP, and permeation of DZP across the membrane. Panel (a) shows DZP permeation across the MDCK-IIwt membrane with active drug applied on the apical side at 70% saturation. Panel (b) shows permeation of DZP across the membrane following administration of AVF/enzyme on the apical side, and panel (c) summarizes DZP flux across the membrane as a function of apical AVF concentration. The abscissa in panel (c) is equal to the supersaturation potential, S, and this graph shows that flux is linearly related to S. Panels (d)-(f) summarize various experiments, which show that apical DZP concentrations rise to peak values that are far above the saturation level, and then fall over the course of 1-2 hours. The prodrug AVF was found not to permeate the membrane significantly, and there was no evidence of formation of DZP precipitates. These studies provide strong evidence that supersaturated DZP solutions, derived enzymatically from AVF, remain in solution without precipitating, and that permeation from these supersaturated solutions far exceeds that of subsaturated solutions. The TEER and inulin permeation experiments indicated that there was no significant disruption of membrane function during these experiments, and this was further confirmed by visual inspection of the membranes at the end of the experiments.

Identical experiments were carried out to measure the permeation of MDZ across the MDCK-II2wt membranes following conversion from MDZ-pro by A.O. protease at high supersaturation potentials. Results of these experiments are analogous to what was demonstrated above for AVF and DZP.

Thus, AVF or MDZ-pro may be co-administered with a converting enzyme that rapidly converts AVF to DZP and MDZ-pro to MDZ, rendering the DZP or MDZ and in a supersaturated state that is rapidly absorbed across the nasal mucosal membrane, (absorption occurs more rapidly than crystallization). This system is expected to cause rapid delivery of DZP or MDZ for effective treatment of status epilepticus (SE) and other neurological emergencies, when administered intranasally.

Synthesis of Avizafone Hydrochloride and a Midazolam L-lysine Prodrug

Synthesis of avizafone hydrochloride. Avizafone is a lysine prodrug of diazepam. For the preparation of avizafone a new method was developed (Kapoor, et al., Rapid Delivery of Diazepam from Supersaturated Solutions Prepared Using Prodrug/Enzyme Mixtures: Toward Intranasal Treatment of Seizure Emergencies. AAPS *Journal* 2014, 16, 577-585). Subsequently it was determined by Mosher amide analysis that the avizafone prepared using this method was a mixture of two enantiomers in a ratio of about 80:20. This result demonstrated that partial racemization had taken place during the synthesis, presumably at peptide coupling step. Therefore, the previously reported method was used (Hassall et al., Phenyl keto derivatives of lysyl glycinamide. 1978-40125, 514778, 19780922, 1981) to prepare avizafone by modifying the protecting groups of lysine. In the original synthesis the benzyloxycarbonyl protecting group was used to protect the nitrogens. The synthesis described below uses a Boc protecting group, which can be cleaved by hydrochloric acid.

The synthesis (Scheme 1) began by coupling aminoketone 3 with in situ generated Z-glycine acid chloride 2 to provide glycine amide 4 in high yield. Benzyloxycarbonyl group deprotection of 4 was carried out with 33% HBr in AcOH to yield the diazepam open form as salt 5 in 77%. The salt 5 was treated with Boc-L-Lys(Boc)-OSu (6) using N-ethylmorpholine as base to obtain the desired di-Boc protected Avizafone derivative 7 (55%) along with diazepam 8 (39%). In the final step, di-Boc protected Avizafone 7 was subjected to deprotection with 4M HCl in dioxane to provide the target compound avizafone hydrochloride (9) in good yield (85%). The enantiopurity of the synthesized Avizafone (9) was determined using the Mosher's method (Strizhak et al., Two-Color Fluorescent L-Amino Acid Mimic of Tryptophan for Probing Peptide-Nucleic Acid Complexes. *Bioconjugate Chemistry* 2012, 23, 2434-2443) by preparing two diastereomers with R- and S-MTPA Cl. The ee of the synthesized compound was determined to be 99% by $^{19}F$ NMR analysis of the Mosher bis-amide derivatives, indicating that no epimerization had occurred during the synthesis.

Scheme 1. Synthesis of Avizafone hydrochloride

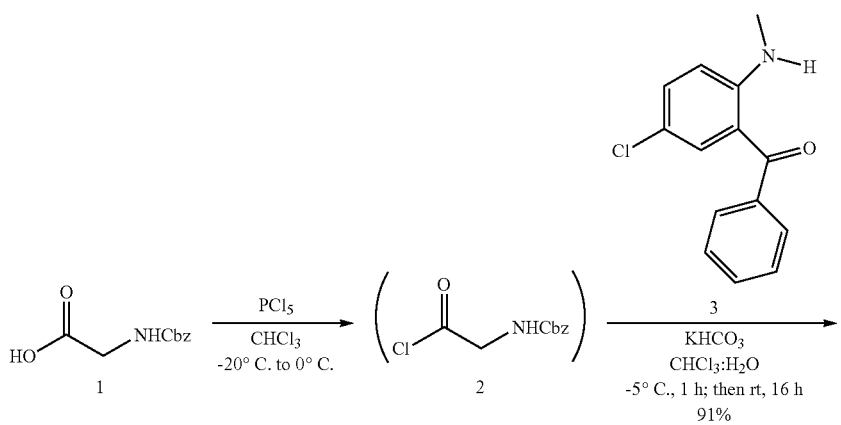

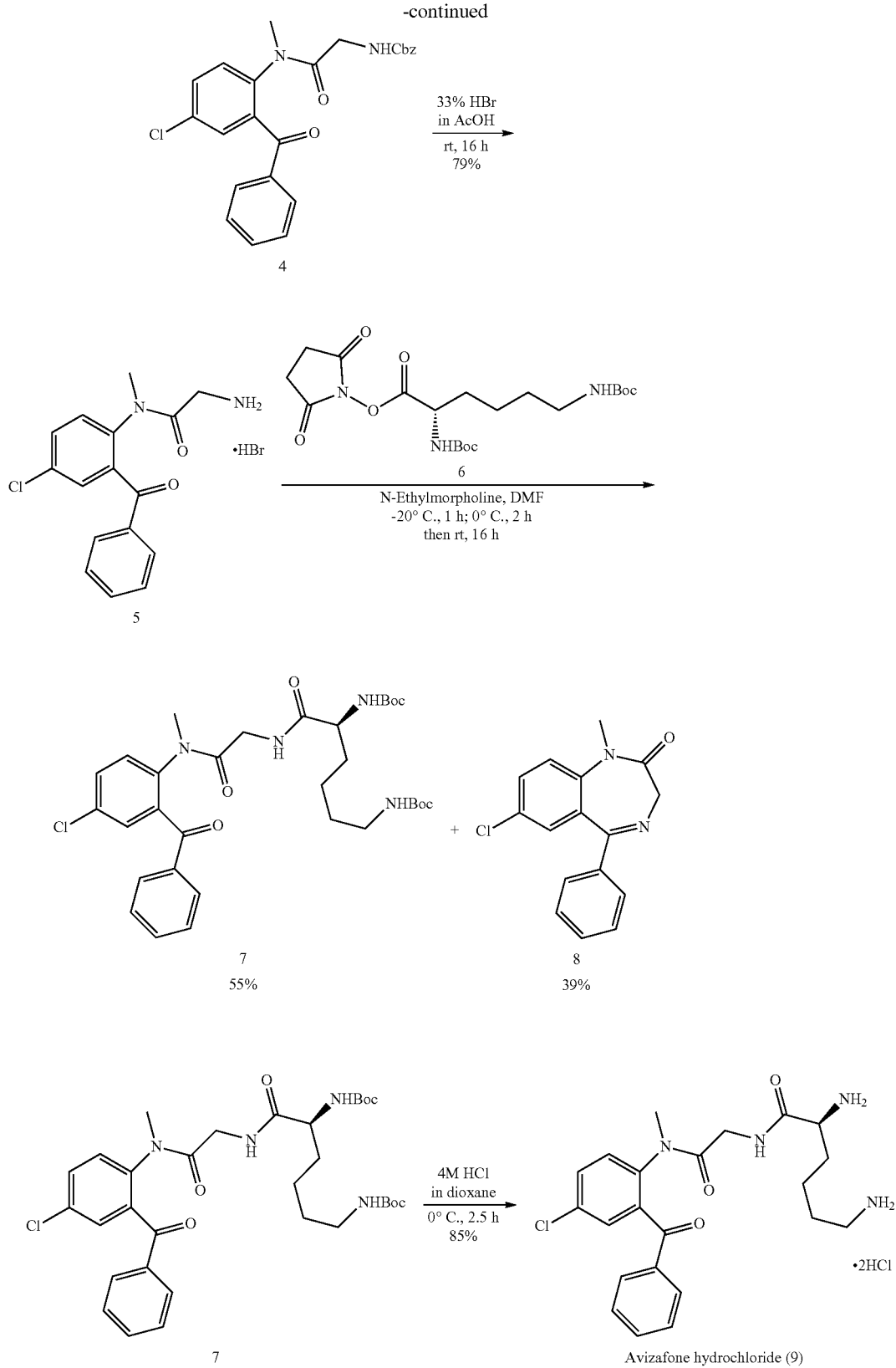
Subsequently, the same coupling and deprotection strategy was applied to the synthesis of the midazolam L-lysine-prodrug 13 (Scheme 2).

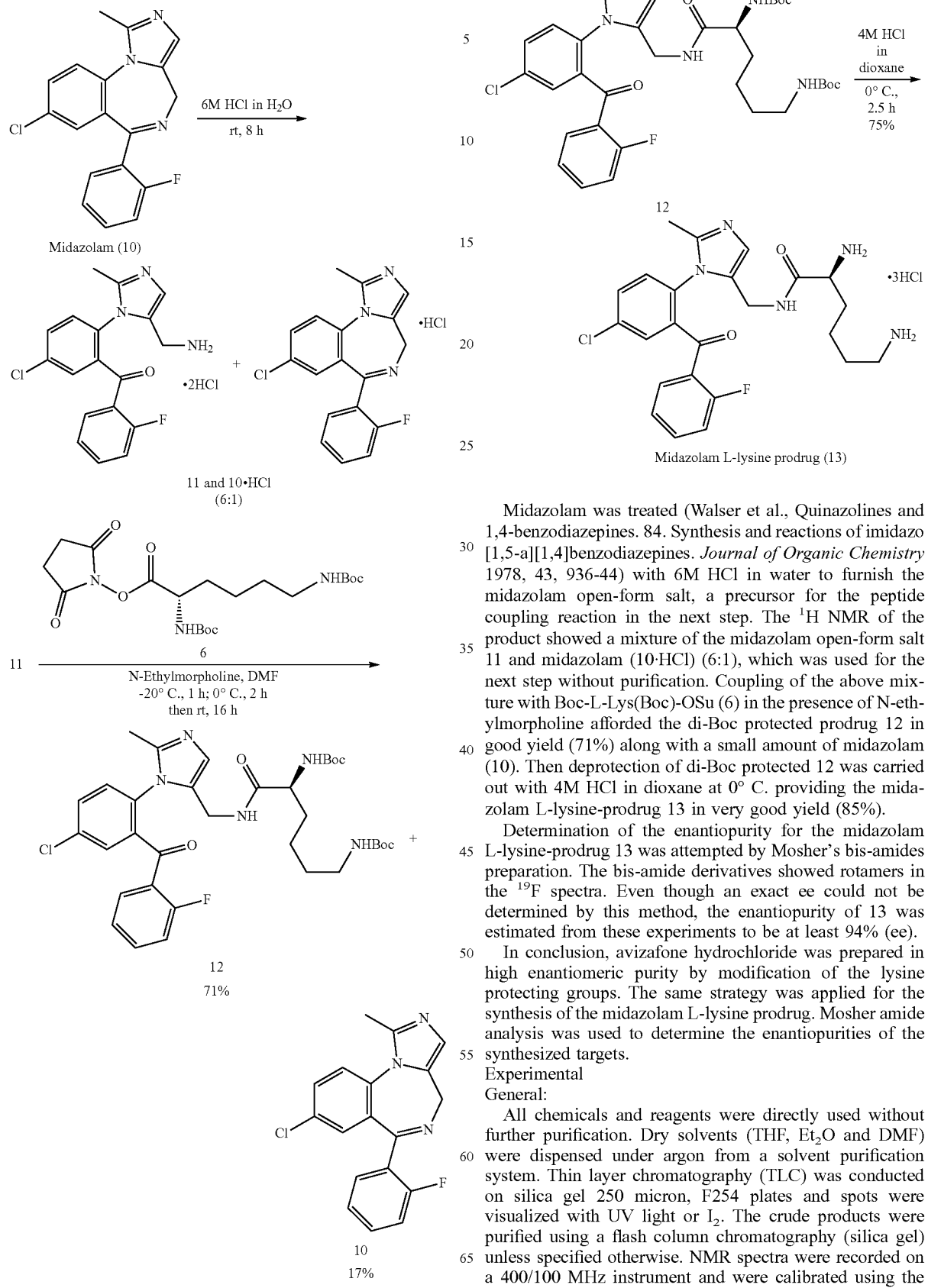

Midazolam was treated (Walser et al., Quinazolines and 1,4-benzodiazepines. 84. Synthesis and reactions of imidazo [1,5-a][1,4]benzodiazepines. *Journal of Organic Chemistry* 1978, 43, 936-44) with 6M HCl in water to furnish the midazolam open-form salt, a precursor for the peptide coupling reaction in the next step. The $^1$H NMR of the product showed a mixture of the midazolam open-form salt 11 and midazolam (10·HCl) (6:1), which was used for the next step without purification. Coupling of the above mixture with Boc-L-Lys(Boc)-OSu (6) in the presence of N-ethylmorpholine afforded the di-Boc protected prodrug 12 in good yield (71%) along with a small amount of midazolam (10). Then deprotection of di-Boc protected 12 was carried out with 4M HCl in dioxane at 0° C. providing the midazolam L-lysine-prodrug 13 in very good yield (85%).

Determination of the enantiopurity for the midazolam L-lysine-prodrug 13 was attempted by Mosher's bis-amides preparation. The bis-amide derivatives showed rotamers in the $^{19}$F spectra. Even though an exact ee could not be determined by this method, the enantiopurity of 13 was estimated from these experiments to be at least 94% (ee).

In conclusion, avizafone hydrochloride was prepared in high enantiomeric purity by modification of the lysine protecting groups. The same strategy was applied for the synthesis of the midazolam L-lysine prodrug. Mosher amide analysis was used to determine the enantiopurities of the synthesized targets.

Experimental

General:

All chemicals and reagents were directly used without further purification. Dry solvents (THF, Et$_2$O and DMF) were dispensed under argon from a solvent purification system. Thin layer chromatography (TLC) was conducted on silica gel 250 micron, F254 plates and spots were visualized with UV light or I$_2$. The crude products were purified using a flash column chromatography (silica gel) unless specified otherwise. NMR spectra were recorded on a 400/100 MHz instrument and were calibrated using the residual undeuterated solvent peaks as an internal reference (CHCl$_3$ @ 7.26 ppm $^1$H-NMR, 77.23 ppm $^{13}$C-NMR, CH$_3$OH @ 4.87 ppm $^1$H-NMR, 48.15 ppm $^{13}$C-NMR and H$_2$O @ 4.80 ppm $^1$H-NMR). The following abbreviations were used to explain NMR peak multiplicities: s=singlet, d=doublet, t=triplet, dd=double doublet, m=multiplet.

Benzyl (2-((2-Benzoyl-4-chlorophenyl)(methyl)amino)-2-oxoethyl)carbamate (4)

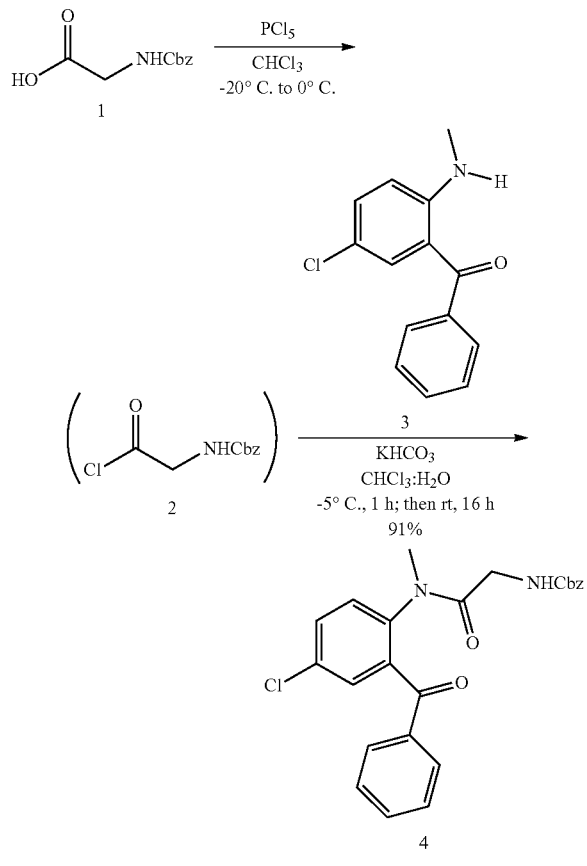

Phosphorous pentachloride (4.41 g, 21.21 mmol) was added portion wise to a suspension of N-benzyloxycarbonyl glycine (1, 4.09 g, 19.58 mmol) in anhydrous CHCl$_3$ (120 mL) at −20° C. After completion of addition, the reaction mixture was warmed to 0° C. The suspension turned clear in five minutes indicating the formation of acid chloride 2. Next, the acid chloride was added dropwise to a second flask containing 5-chloro-2-methylaminobenzophenone (3, 4.01 g, 16.32 mmol), KHCO$_3$ (16.81 g, 168.10 mmol), CHCl$_3$ (120 mL), and water (150 mL) at −5° C. The reaction mixture was stirred for 1 h at the same temperature and 16 h at room temperature. Thin layer chromatography indicated complete consumption of the starting material. The organic phase was separated and the aqueous phase was extracted with CHCl$_3$ (2×100 mL). The combined organic fractions were dried over Na$_2$SO$_4$, filtered, and evaporated in vacuo. The crude residue was purified by flash column chromatography (silica gel, 0-50% ethyl acetate in hexanes) to give 4 (6.51 g, 91%) as brown gum. The presence of rotamers precluded a comprehensive assignment of all proton and carbon resonances. R$_f$ 0.50 (hexanes/ethyl acetate, 1:1); $^1$H NMR (400 MHz, CDCl$_3$) δ7.76 (t, J=8.7 Hz, 2H), 7.62 (t, J=7.4 Hz, 0.83H), 7.57 (dt, J=10.0, 3.5 Hz, 1H), 7.53-7.40 (m, 3.36H), 7.32 (dd, J=8.2, 6.3 Hz, 5.82H), 7.21 (d, J=8.5 Hz, 0.25H), 5.62 (t, J=4.5 Hz, 0.69H), 5.53 (s, 0.2H), 5.07 (s, 2H), 3.83 (dd, J=17.2, 5.5 Hz, 1H), 3.70 (dd, J=16.9, 3.7 Hz, 1H), 3.24 (s, 0.63H), 3.05 (s, 2.38H); $^{13}$C NMR (100 MHz, CDCl$_3$) S 194.58, 193.48, 168.82, 156.27, 140.28, 139.03, 138.81, 138.26, 136.63, 136.50, 135.96, 134.76, 134.42, 133.61, 133.07, 132.51, 132.09, 131.16, 130.19, 130.08, 129.07, 128.63, 128.17, 66.95, 43.64, 38.08, 37.67; HRMS (ESI+) calculated for C$_{24}$H$_{21}$ClN$_2$O$_4$ [M+Na$^+$] 459.1082, found 459.1068.

2-Amino-N-(2-benzoyl-4-chlorophenyl)-N-methyl-acetamide Hydrobromide (5)

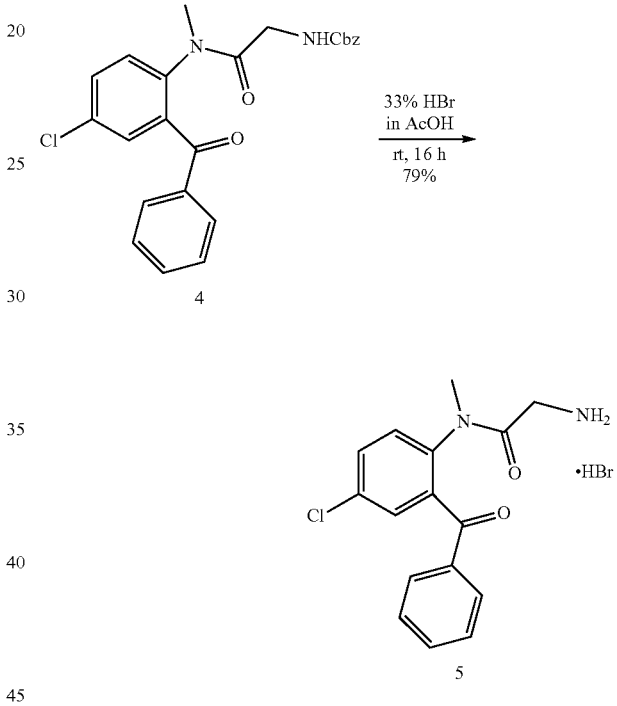

To compound 4 (5.01 g, mmol) was added HBr (33%) in AcOH (15 mL) at room temperature under nitrogen. The resulting solution was stirred for 16 h, then diethyl ether (200 mL) was added slowly with stirring until a precipitate formed. The precipitate was filtered and then washed with a minimum amount of acetone and diethyl ether to provide salt 5 (3.50 g, 79%) as colorless powder. The presence of rotamers precluded a comprehensive assignment of all proton and carbon resonances; mp 196-197° C. (decomposition) (lit 194-195° C.) (Hassall et al., Phenyl keto derivatives of lysyl glycinamide. 1978-40125, 514778, 19780922, 1981); $^1$H NMR δ (400 MHz, D$_2$O) δ7.88-7.83 (m, 1.2H), 7.79 (ddt, J=11.1, 8.9, 2.2 Hz, 2.8H), 7.68 (dd, J=12.1, 2.4 Hz, 1H), 7.64-7.55 (m, 2.6H), 7.46 (d, J=8.6 Hz, 0.4H), 3.87-3.65 (m, 2H), 3.22 (s, 1.2H), 3.04 (s, 1.8H); $^{13}$C NMR δ (100 MHz, D$_2$O) 197.02, 177.37, 168.45, 167.39, 143.79, 136.93, 136.85, 135.98, 135.62, 135.06, 134.87, 133.41, 133.27, 132.00, 131.06, 130.75, 130.32, 129.74, 128.97, 124.91, 124.65, 50.17, 36.02; HRMS (ESI+) calculated for C$_{16}$H$_{15}$ClN$_2$O$_2$ [M+H$^+$] 303.0895, found 303.0886.

Di-tert-butyl (6-((2-((2-Benzoyl-4-chlorophenyl)(methyl)amino)-2-oxoethyl)amino)-6-oxohexane-1,5-diyl)(S)-dicarbamate (7)

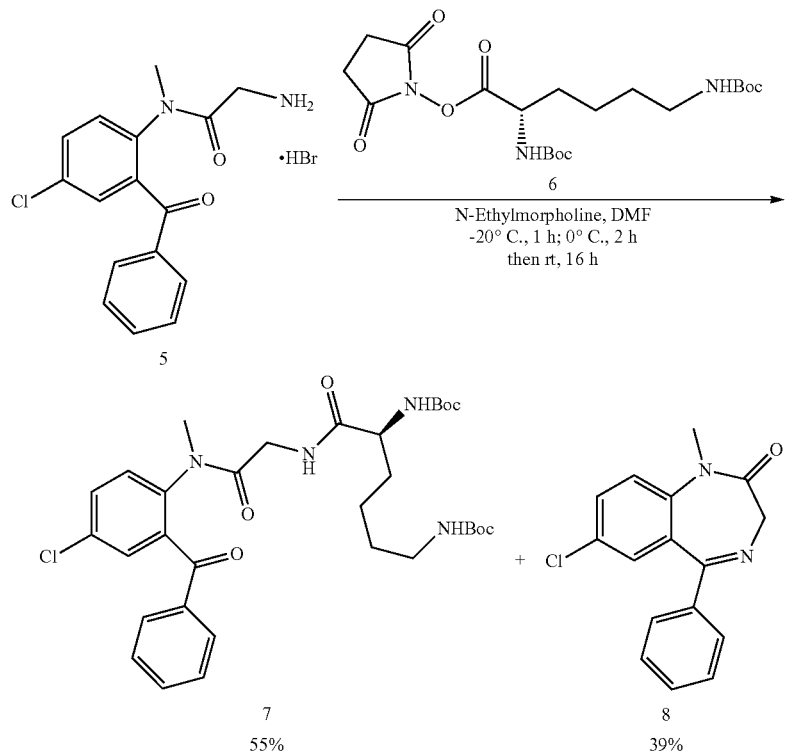

To aminoketone 5 (2.50 g, 6.52 mmol) and Boc-L-Lys(Boc)-OSu (6, 2.90 g, 6.52 mmol) in dry DMF (60 mL) was added N-ethylmorpholine (0.825 mL, 6.52 mmol) at −20° C. under nitrogen. The reaction mixture was stirred for 1 h at the same temperature and 2 h at 0° C., then stirring was continued for 16 h at room temperature. The reaction was diluted with ethyl acetate (150 mL), washed with water (2×100 mL), brine (100 mL), dried over $Na_2SO_4$, filtered and then the volatiles were evaporated in vacuo. The crude residue was purified by flash column chromatography (silica gel, 0-75% ethyl acetate in hexanes) to furnish 7 (2.26 g, 55%) as a colorless powder and diazepam (8, 722 mg, 39%) as a colorless powder.

Compound 7: The presence of rotamers precluded a comprehensive assignment of all proton and carbon resonances. $R_f$ 0.53 (hexanes/ethyl acetate, 1:1); $^1$H NMR (400 MHz, $CDCl_3$) δ7.79-7.71 (m, 2H), 7.66-7.41 (m, 5H), 7.32 (dd, J=8.4, 4.2 Hz, 0.79H), 7.21 (d, J=8.5 Hz, 0.21H), 6.81 (dt, J=9.7, 4.6 Hz, 0.76H), 6.69 (d, J=4.3 Hz, 0.19H), 5.11 (s, 1H), 4.81-4.54 (m, 1H), 4.09 (dt, J=7.1, 3.7 Hz, 1H), 3.89 (dd, J=17.4, 5.2 Hz, 1H), 3.68 (dd, J=17.4, 3.7 Hz, 1H), 3.24 (s, 0.63H), 3.04 (s, 4.34H), 1.86-1.71 (m, 1H), 1.66-1.53 (m, 1H), 1.52-1.24 (m, 22H); $^{13}$C NMR (100 MHz, $CDCl_3$) δ194.54, 193.47, 172.00, 168.67, 156.26, 155.72, 140.24, 139.02, 138.68, 138.20, 136.57, 135.97, 134.84, 134.46, 133.65, 133.16, 132.63, 132.17, 131.25, 130.25, 129.11, 128.63, 80.11, 79.18, 54.48, 42.24, 41.68, 40.24, 38.17, 37.73, 32.70, 29.81, 28.59, 22.73; HRMS (ESI+) calculated for $C_{32}H_{43}ClN_4O_7$ [M+Na$^+$] 653.2712, found 653.2710; $[\alpha]_D^{22}$ −10.6 (c=0.5, $CH_3OH$).

Compound 8: $R_f$ 0.24 (hexanes/ethyl acetate, 1:1); mp 126-130° C. (lit 129-131.5° C.) (Gates, M., New synthesis of diazepam. *Journal of Organic Chemistry* 1980, 45, 1675-81); $^1$H NMR (400 MHz, CDCl$_3$) δ7.62-7.58 (m, 2H), 7.53-7.45 (m, 2H), 7.41 (dd, J=8.2, 6.6 Hz, 2H), 7.31-7.27 (m, 2H), 4.83 (d, J=10.8 Hz, 1H), 3.77 (d, J=10.8 Hz, 1H), 3.39 (s, 3H); $^{13}$C NMR (101 MHz, CDCl$_3$) δ170.13, 169.11, 142.80, 138.37, 131.65, 130.89, 130.27, 130.09, 129.66, 129.46, 128.60, 122.71, 57.18, 35.07; HRMS (ESI+) calculated for $C_{16}H_{13}ClN_2O$ [M+H$^+$] 285.0789, found 285.0788.

Avizafone Hydrochloride (9)

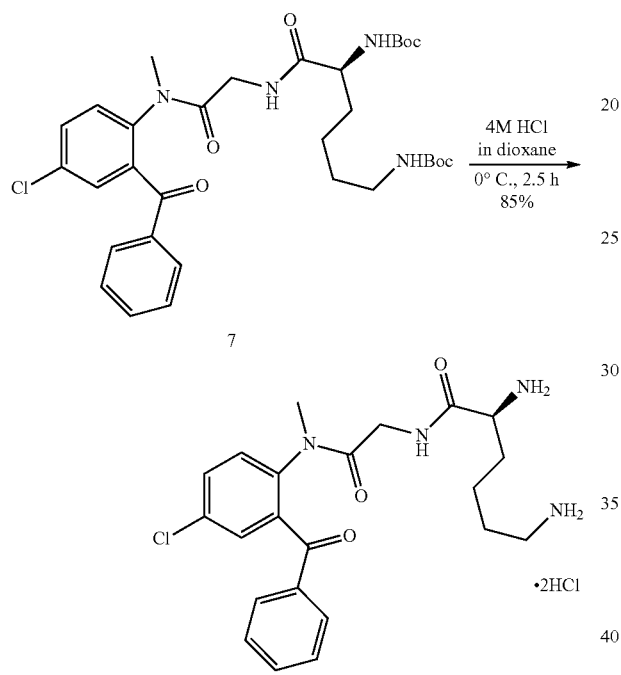

Avizafone hydrochloride (9)

To compound 7 (1.01 g, 1.6 mmol) was added 4M HCl in dioxane (20 mL) at 0° C. under nitrogen and stirred for 2.5 h at the same temperature. Volatiles were carefully evaporated in vacuo at room temperature, then diethyl ether (30 mL) was added to the residue and filtered under nitrogen pressure. Additional washings with diethyl ether under nitrogen pressure filtration resulted in the formation of avizafone hydrochloride (9, 680 mg, 85%) as a colorless powder (hygroscopic and light sensitive). The presence of rotamers precluded a comprehensive assignment of all proton and carbon resonances; $^1$H NMR (400 MHz, D$_2$O) δ7.93-7.67 (m, 5H), 7.60 (h, J=5.1, 3.8 Hz, 2H), 7.44 (d, J=8.6 Hz, 0H), 4.13-3.71 (m, 3H), 3.24 (s, 1H), 3.13-2.88 (m, 4H), 2.02-1.82 (m, 2H), 1.71 (dq, J=21.9, 7.7 Hz, 2H), 1.48 (dp, J=22.5, 8.0, 7.6 Hz, 2H); $^{13}$C NMR (101 MHz, D$_2$O) δ197.88, 197.48, 170.37, 170.26, 170.06, 169.90, 139.41, 138.11, 138.03, 137.03, 136.64, 136.01, 135.84, 134.94, 134.57, 134.38, 133.18, 132.99, 130.61, 130.17, 129.69, 129.55, 128.95, 128.74, 128.33, 52.93, 52.84, 41.90, 41.81, 40.83, 38.94, 37.60, 37.26, 30.23, 26.27, 20.95; HRMS (ESI+) calculated for $C_{22}H_{27}ClN_4O_3$ [M+H$^+$] 431.1844, found 431.1856; $[\alpha]_D^{22}$+19.2 (c=0.5, CH$_3$OH).

Determination of the Enantiopurity of Avizafone by Mosher's Method

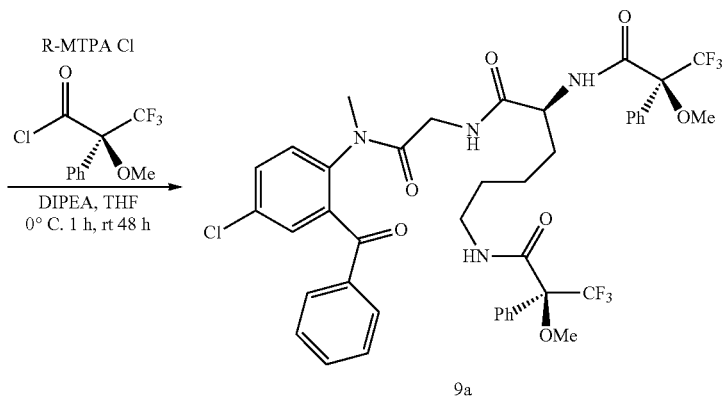

9a

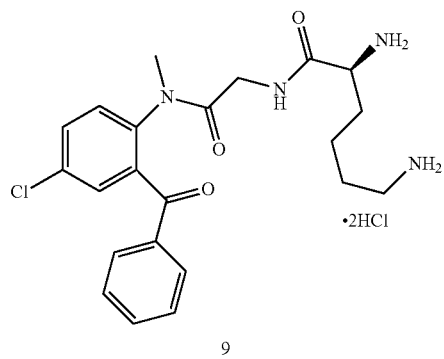

9

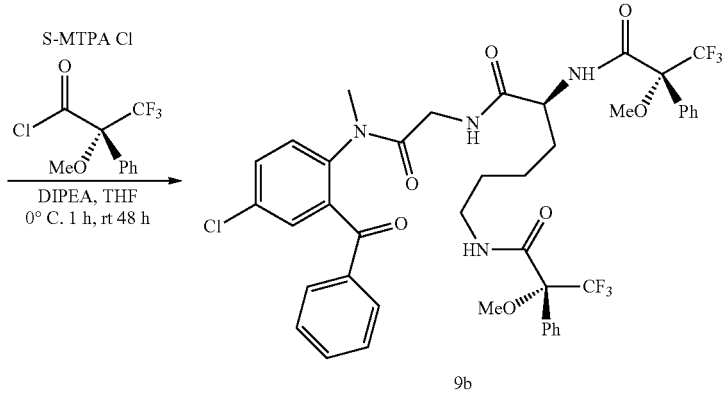

9b

General procedure for Avizafone Mosher bis-amide synthesis (Strizhak et al., Two-Color Fluorescent L-Amino Acid Mimic of Tryptophan for Probing Peptide-Nucleic Acid Complexes. *Bioconjugate Chemistry* 2012, 23, 2434-2443):

To avizafone hydrochloride (9, 15 mg) in THF (2 mL) were added R- or S-MTPA Cl (30 mg, 4 eq) in THF (1 mL) and DIPEA (36 µL, 7 eq) under nitrogen at 0° C. After stirring for 1 h at the same temperature, the reaction mixture was stirred for 48 h at room temperature. Water (5 mL) was added to the reaction mixture and stirred for an additional 1 h to hydrolyze the excess MTPA-Cl. The reaction was extracted with ethyl acetate (3×5 mL). The combined organic fractions were washed with saturated NaHCO$_3$ (5 mL), 1 N HCl (5 mL) and brine (5 mL). Volatiles were evaporated in vacuo and the crude residue was purified by flash column chromatography (silica gel). $^{19}$F spectra were recorded for the derivatives. 9a: $^{19}$F NMR (376 MHz, CDCl$_3$) δ68.64 (major, CHNH amide), 68.85 (CH$_2$NH amide), 69.04 (minor, CHNH amide); 99% ee. 9b: $^{19}$F NMR (376 MHz, CDCl$_3$) δ68.64 (minor, CHNH amide), 68.88 (CH$_2$NH amide), 69.03 (major, CHNH amide); 99% ee.

35

(2-(5-(Aminomethyl)-2-methyl-1H-imidazol-1-yl)-5-chlorophenyl)(2-fluorophenyl)methanone Dihydrochloride (11)

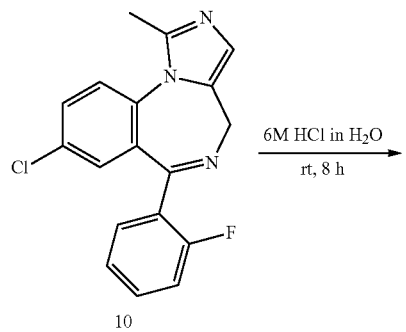

36

Di-tert-butyl (6-(((1-(4-Chloro-2-(2-fluorobenzoyl)phenyl)-2-methyl-1H-imidazol-5-yl)methyl)amino)-6-oxohexane-1,5-diyl)(S)-dicarbamate (12)

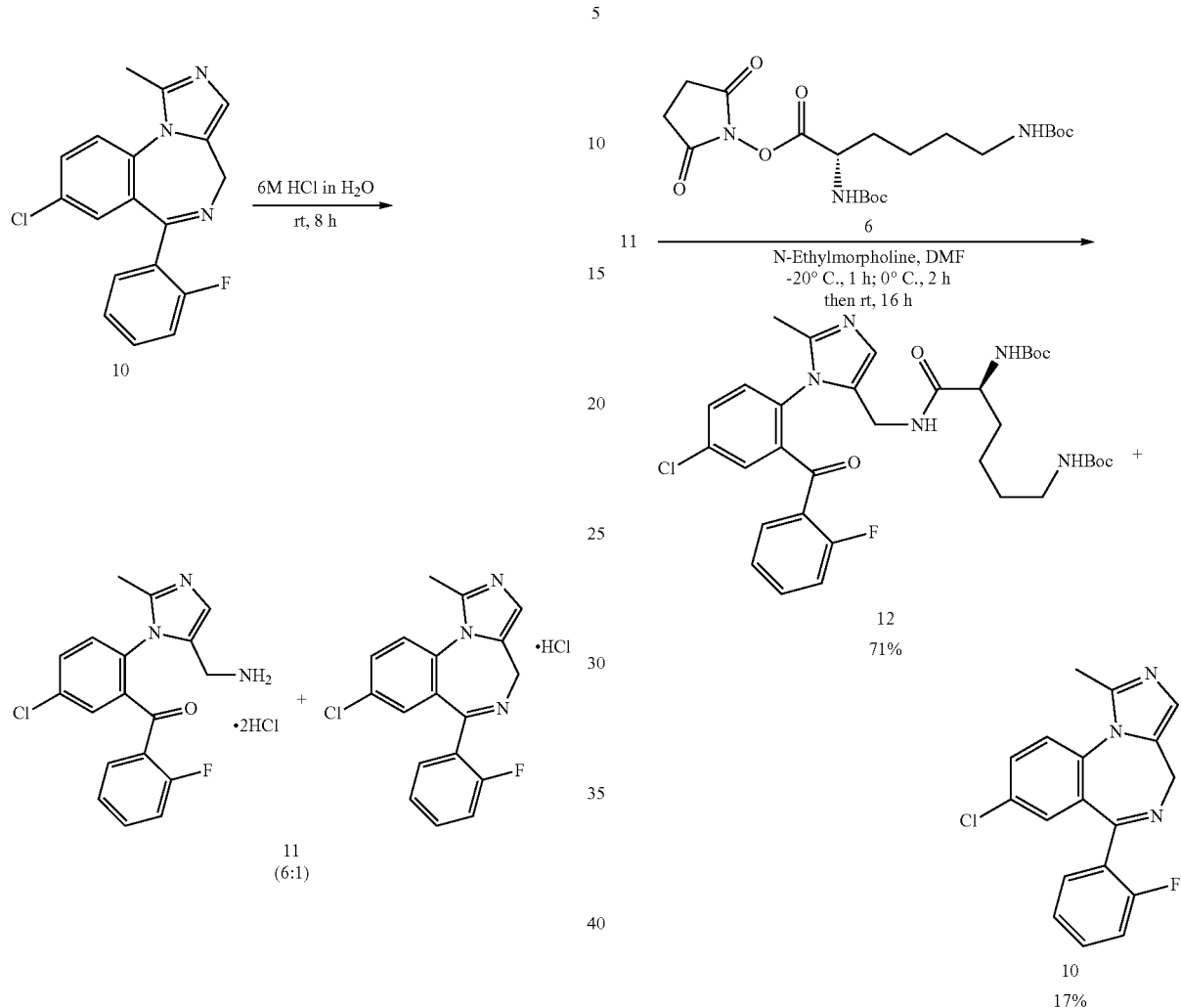

Midazolam (10, 0.50 g) was taken into 6M HCl in $H_2O$ (6 mL) and allowed to stand for 8 h at room temperature. Isopropanol (15 mL) was added to the solution and partially evaporated in vacuo at room temperature. The operation was repeated twice, then diethyl ether (25 mL) was added and the flask was kept in the refrigerator overnight. Precipitated crystalline material was filtered and washed with diethyl ether to provide a 6:1 mixture of the midazolam ring-open form 11 and the midazolam hydrochloric acid salt (10·HCl). The mixture was used for the next step without further purification. $^1$H NMR (400 MHz, $D_2O$) δ8.05-7.96 (m, 2H), 7.92 (dd, J=8.7, 2.5 Hz, 0.17H), 7.84-7.63 (m, 4.38H), 7.63-7.54 (m, 0.48H), 7.41 (t, J=7.5 Hz, 1.13H), 7.32 (dd, J=11.1, 8.4 Hz, 1H), 7.25 (dd, J=11.1, 8.5 Hz, 0.17H), 5.21 (d, J=14.0 Hz, 0.16H), 4.39 (d, J=13.6 Hz, 0.19H), 4.19 (s, 2H), 2.85 (s, 0.45H), 2.46 (s, 3H); $^{13}$C NMR (100 MHz, $D_2O$) δ192.48, 162.17, 159.64, 147.62, 138.29, 137.12, 136.83, 134.67, 132.57, 131.68, 131.64, 128.41, 127.22, 125.08, 123.95, 118.82, 116.90, 116.78, 43.04, 32.26, 10.48.

To the mixture of 11 and 10·HCl (0.60 g, 1.44 mmol) and Boc-L-Lys(Boc)-OSu (6) (0.638 g, 1.44 mmol) in dry DMF (15 mL) was added N-ethylmorpholine (0.33 mL, 6.52 mmol) at −20° C. under nitrogen. The reaction was stirred for 1 h at the same temperature and 2 h at 0° C., then stirred at room temperature for 16 h. The reaction was diluted with ethyl acetate (50 mL), washed with water (2×50 mL), brine (50 mL), dried over $Na_2SO_4$, filtered and the volatiles were evaporated in vacuo. The crude residue was purified by flash column chromatography (silica gel, 0-5% methanol in dichloromethane) to provide 12 (687 mg, 71%, as a colorless powder) and midazolam (10) (80 mg, 17%, colorless powder).

Compound 12: The presence of rotamers precluded a comprehensive assignment of all proton and carbon resonances. $R_f$ 0.10 (dichloromethane/methanol, 95:5); $^1$H NMR (400 MHz, $CD_3OD$) δ7.85-7.72 (m, 2H), 7.62 (dtd, J=7.7, 5.4, 2.6 Hz, 2H), 7.51 (dd, J=14.8, 8.4 Hz, 1H), 7.31-7.25 (m, 1H), 7.19 (dd, J=10.8, 8.4 Hz, 1H), 6.75 (d, J=4.5 Hz, 1H), 6.68-6.52 (m, 1H), 4.19 (d, J=15.6 Hz, 1H), 4.01 (dd, J=15.6, 7.5 Hz, 1H), 3.94-3.83 (m, 1H), 3.02 (td, J=6.8, 3.3 Hz, 2H), 2.09 (s, 3H), 1.66-1.58 (m, 1H), 1.45 (dd, J=12.0, 5.5 Hz, 23H); $^{13}$C NMR (101 MHz, CD$_3$OD) δ192.25, 174.91, 163.47, 160.94, 158.72, 157.98, 147.56, 141.21, 137.28, 136.93, 134.17, 133.21, 132.64, 132.34, 131.33, 127.25, 126.70, 126.12, 117.80, 117.56, 80.79, 80.00, 56.37, 56.08, 41.08, 34.47, 33.14, 32.94, 30.71, 28.94, 24.30, 13.32; HRMS (ESI+) calculated for C$_{34}$H$_{43}$ClFN$_5$O$_6$[M+H$^+$] 672.2959, found 672.2954; [α]$_D^{22}$ −29.8 (c=0.5, CH$_3$OH).

Compound 10: R$_f$ 0.19 (dichloromethane/methanol, 95:5); mp 155-157° C. (lit 158-160° C.) (Walser et al., Quinazolines and 1,4-benzodiazepines. 84. Synthesis and reactions of imidazo[1,5-a][1,4]benzodiazepines. *Journal of Organic Chemistry* 1978, 43, 936-44); $^1$H NMR (400 MHz, CDCl$_3$) δ7.62 (td, J=7.6, 1.8 Hz, 1H), 7.55 (dd, J=8.6, 2.4 Hz, 1H), 7.48-7.36 (m, 2H), 7.27-7.19 (m, 2H), 7.05-6.98 (m, 1H), 6.93 (s, 1H), 5.12 (d, J=12.9 Hz, 1H), 4.04 (d, J=12.9 Hz, 1H), 2.55 (s, 3H); $^{13}$C NMR (101 MHz, CDCl$_3$) δ164.58, 161.79, 159.29, 144.34, 134.46, 133.84, 132.82, 132.51, 132.19, 131.20, 129.73, 127.77, 125.88, 124.70, 124.12, 116.61, 46.28, 15.16; HRMS (ESI+) calculated for C$_{18}$H$_{13}$ClFN$_3$ [M+H$^+$] 326.0855, found 326.0842.

lp;2p

Midazolam L-Lysine Prodrug (13)

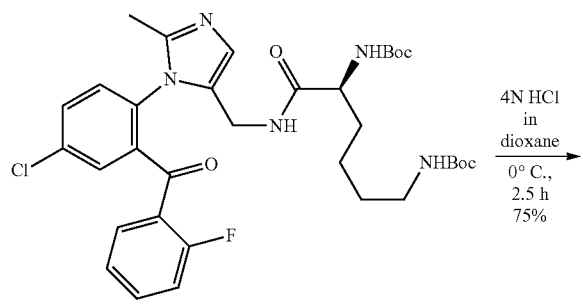

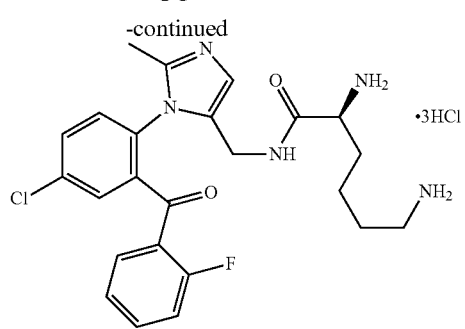

Midazolam L-lysine prodrug (13)

To compound 12 (100 mg, 0.14 mmol) was added 4M HCl in dioxane (5 mL) at 0° C. under nitrogen and the resulting solution was stirred for 2.5 h at the same temperature. The volatiles were evaporated in vacuo at room temperature and the initially obtained residue was washed with diethyl ether using nitrogen pressure filtration to provide the midazolam L-lysine prodrug 13 (60 mg, 75%) as a colorless powder (hygroscopic and light sensitive). The presence of rotamers precluded a comprehensive assignment of all proton and carbon resonances; $^1$H NMR (400 MHz, D$_2$O) δ8.04-7.99 (m, 2H), 7.83-7.64 (m, 3H), 7.48 (s, 1H), 7.41 (t, J=7.6 Hz, 1H), 7.33 (t, J=9.8 Hz, 1H), 4.33 (d, J=15.5 Hz, 2H), 3.97-3.88 (m, 1H), 3.05-2.94 (m, 2H), 2.44 (d, J=5.0 Hz, 3H), 1.86-1.74 (m, 2H), 1.68 (td, J=7.9, 4.5 Hz, 2H), 1.38 (q, J=7.9 Hz, 2H); $^{13}$C NMR (101 MHz, D$_2$O) δ192.43, 169.53, 159.34, 146.82, 146.58, 136.59, 136.30, 134.53, 132.72, 131.50, 131.19, 130.93, 128.22, 125.05, 124.23, 117.51, 117.28, 116.98, 52.88, 38.92, 32.85, 30.25, 26.30, 21.32, 10.62; HRMS (ESI+) calculated for C$_{24}$H$_{27}$ClFN$_5$O$_2$ [M+H$^+$] 472.1910, found 472.1927; [α]$_D^{22}$ +21.4° (c=0.5, CH$_3$OH).

Determination of the Enantiopurity of 13 by Mosher's Method

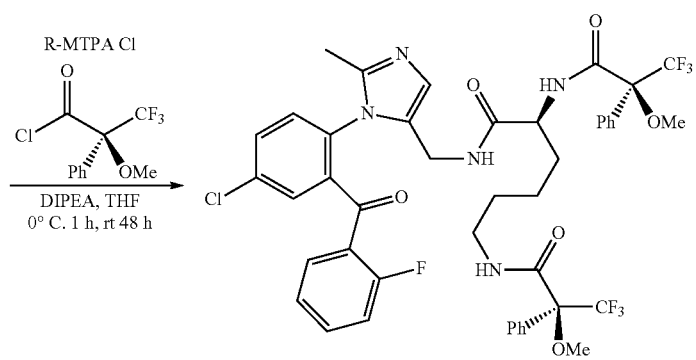

13a

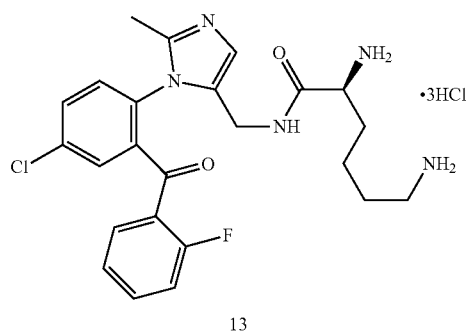

13

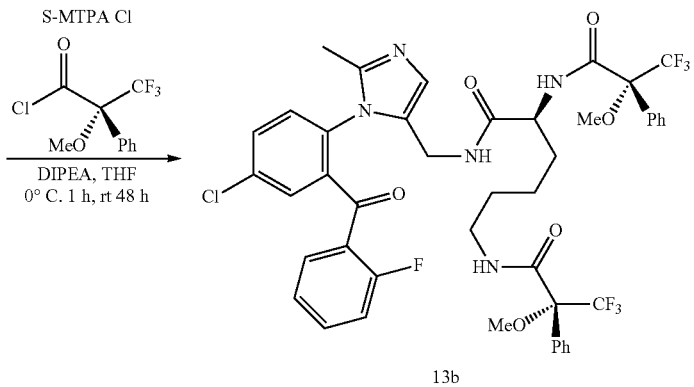

13b

General Procedure for Midazolam L-Lysine-Prodrug Mosher's Bis-Amide Synthesis To midazolam L-lysine hydrochloride (13, 10 mg) in THF (2 mL) were added R- or S-MTPA Cl (17 mg, 4 eq) in THF (1 mL) and DIPEA (24 μL, 8 eq) under nitrogen at 0° C. After stirring for 1 h at the same temperature, the reaction mixture was stirred for 48 h at room temperature. Water (5 mL) was added to the reaction mixture and stirred for an additional 1 h to hydrolyze the excess MTPA-Cl. The reaction was extracted with ethyl acetate (3×5 mL). The combined organic fractions were washed with saturated NaHCO$_3$ (5 mL), 1 N HCl (5 mL), NaHCO$_3$ (5 mL) (to avoid the salt formation) and brine (5 mL). Volatiles were evaporated in vacuo and the crude residue was purified by flash column chromatography (silica gel). 13a: $^{19}$F NMR (376 MHz, CDCl$_3$) δ68.56 & 68.68 (major-rotamers, CHNH amide), 68.78 & 68.80 (rotamers, CH$_2$NH amide); did not show a peak for minor enantiomer. 13b: $^{19}$F NMR (376 MHz, CDCl$_3$) δ68.57 and 68.69 (minor-rotamers, CHNH amide), 68.83 (CH$_2$NH amide), 68.92 & 68.95 (major-rotamers, CHNH amide).

EXAMPLE 2

Materials and Methods

Materials.

DZP, MDZ, phenytoin (internal standard or I.S.), A.O. protease (*Aspergillus Oryzae*, 1474.47 U/mL, cat # P6110), and chemicals used for 'cell assay buffer' pH 7.4 (122 mM NaCl, 25 mM NaHCO$_3$, 10 mM glucose, 10 mM HEPES, 3 mM KCl, 1.2 mM MgSO$_4$, 1.4 mM CaCl$_2$, and 0.4 mM K$_2$HPO$_4$) were purchased from Sigma. Lucifer yellow, HPLC grade methanol, acetonitrile and water, were purchased from Fisher Scientific. Dulbecco's modified Eagle's medium, antibiotics, and fetal bovine serum, were purchased from Invitrogen. Madin-Darby canine kidney-II wild type cells (MDCKII-wt) cells were generously provided by Dr. Alfred Schinkel (The Netherlands Cancer Institute, Amsterdam).

Synthesis and Characterization of Prodrugs.

AVF$_m$ (mixture of R- and S-enantiomers) was synthesized as previously described (Kapoor M, et al., *AAPS J*, 2014, 16, 3, 577-585). AVF$_p$ (S-enantiomer of AVF) was synthesized by reacting (5-chloro-2-(methylamino)phenyl) (phenyl) methanone, first with a glycine derivative and then with a lysine derivative to form a lysine-glycine dipeptide side chain. MDZ-pro was produced from MDZ by opening the diazepine ring and adding a lysine group.

Enzyme Kinetics. To determine the enzyme kinetic parameters K$_M$ and V$_{max}$ for a prodrug/enzyme system, various concentrations of prodrug were incubated in assay buffer, pH 7.4 containing A.O. protease, at 32° C., for a fixed time period t, at which point the reaction was stopped using methanol as an enzyme denaturant. Conversion from prodrug to active drug for each initial prodrug concentration was determined by HPLC. The reactions were carried out to times when there was already substantial conversion. Concentrations of product, C$_d$(t) were fit against initial prodrug concentrations, C$_p$ (0), using the integrated Michaelis-Menten equation:

$$C_d(t)+K_M \ln[1-C_d(t)/C_p(0)]=V_{max}t \tag{1}$$

Fitting was carried out using the Matlab nlinfit function (Mathworks).

Cell Monolayers.

Following previously published procedures (Kapoor M, et al., *AAPS J*, 2014, 16, 3, 577-585; and Kapoor M, et al., *Mol Pharm*, 2013, 10, 9, 519-3524), Madin Darby canine kidney II wild type (MDCKII-wt: passages between 10 and 20) cells were cultured and grown as monolayers in 12-well Transwell plates (0.4 mm pore size, polyester, Corning).

Transepithelial electrical resistance (TEER) was measured to assure membrane integrity just prior to conversion/permeation experiments. TEER and a Lucifer yellow dye permeability assay were used to reassess monolayer integrity at the conclusion of each experiment.

HPLC.

The HPLC method for analyzing AVF and DZP is published elsewhere (Kapoor M, et al., AAPS J, 2014, 16, 3, 577-585). MDZ-pro and MDZ concentrations were analyzed using HPLC (Beckman Coulter SYSTEM GOLD: solvent module 126, autosampler 508 and UV detector 166 with 32.0 Karat software v5). The mobile phase was 50 mM monobasic potassium phosphate (containing 0.2% diethylamine) and acetonitrile (30:70 v/v), and the flow rate was 2 mL/min. For analysis, a 50 µL sample (containing 4 µg/mL internal standard) was injected onto a Supercosil LC-18 column (250×4.6 mm, 5 µm particle size) and chromatograms were obtained at 220 nm. The drug peak was normalized by an internal standard (phenytoin) peak area and converted to drug concentration using a calibration curve.

Supersaturated MDZ Solutions.

Appropriate molar concentrations of MDZ-pro equivalent to supersaturated MDZ solution were incubated with the converting enzyme in assay buffer, pH 7.4 at 32° C. (nasal temperature). Supersaturation potential, S, was calculated as the ratio between the molar concentration of administered MDZ-pro and the molar concentration of saturated MDZ:

$$S = \frac{\text{Initial } [MDZ\text{-}pro]}{\text{Saturated } [MDZ]}$$

This is the degree of supersaturation that would be attained if enzymatic conversion on MDZ-pro to MDZ was immediate and without precipitation.

Statistics.

For multiple comparisons, one-way ANOVA with Dunnett's post hoc test was used.

Results

Synthesis and Characterization of Chirally Pure Prodrugs AVFp and MDZ-Pro.

The structures of the HCl salts of AVF and MDZ-pro are shown below. $AVF_p$ and MDZ-pro were synthesized with high enantiomeric purity in 99% ee and 94% ee, respectively. The enantiomeric ratio for $AVF_m$ was 74:26 er. The enantiomeric purity of these compounds was determined by Mosher's method (Hoye T R, Jeffrey C S, Shao F, Nat Protoc, 2007, 2, 2451-2458).

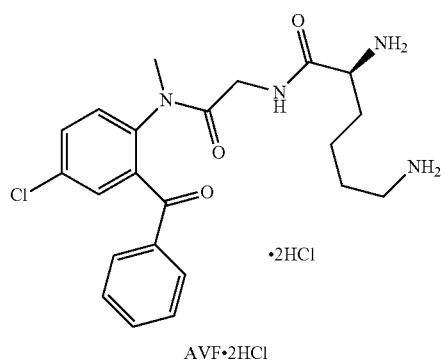

AVF·2HCl

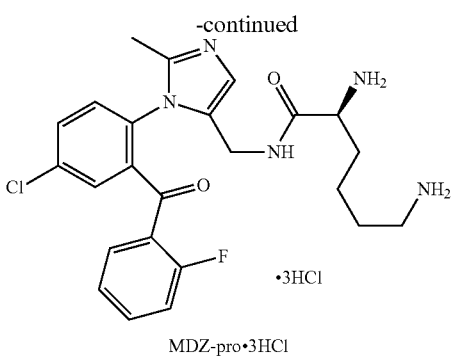

MDZ-pro·3HCl $AVF_p$/A.O. Protease System

Enzyme Kinetics.

Figure 3:
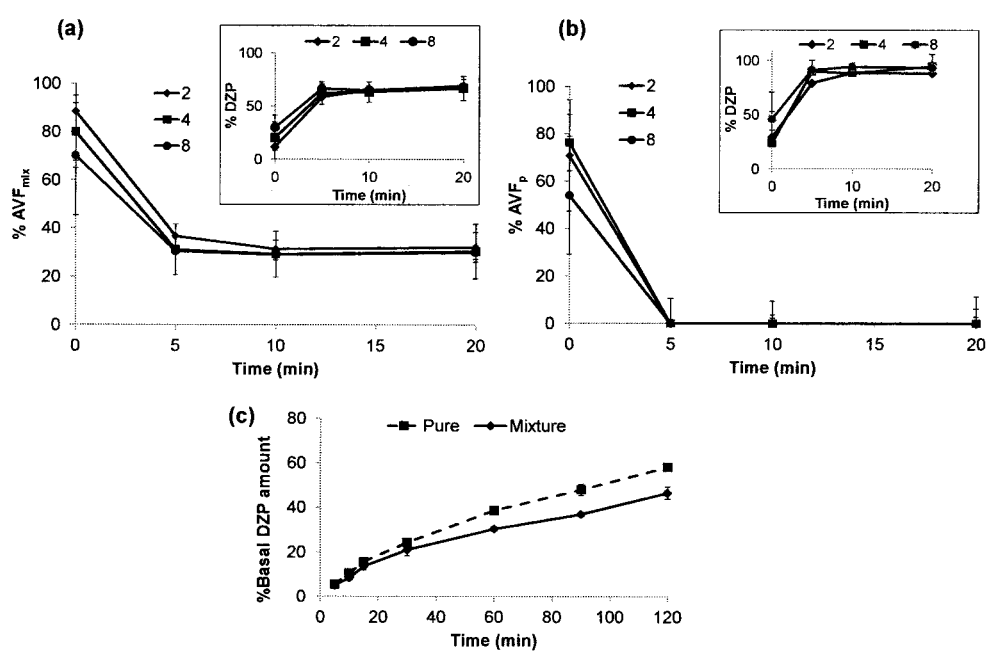
FIG. 3. Reaction kinetics of (a) enantiomeric mixture AVF ($AVF_m$) and (b) chirally pure AVF ($AVF_p$) when incubated with A.O protease (2, 4, 8 U/mL) at 480 μM in assay buffer pH 7.4 at 32° C. (c) Membrane permeation kinetics showing % basal DZP amount when either $AVF_m$ or $AVF_p$ (900 μM) was incubated with A.O protease (4 U/mL) on the apical side of MDCKII-wt monolayers in assay buffer pH 7.4 at 32° C. Mean±SD. n=2.

$AVF_m$ and $AVF_p$ (each at 480 µM) were incubated with A.O. protease (2-8 U/mL) in assay buffer over various time intervals in assay buffer pH 7.4 at 32° C. As shown in FIGS. 3a and 3b and their respective insets, the conversion process, at these enzyme concentrations, was essentially complete in 5 min. However, 100% conversion was observed only with $AVF_p$, while only ~70% of $AVF_m$ was converted. The apparent nonzero conversion observed at time zero is due to a transfer/quench delay.

Figure 4:
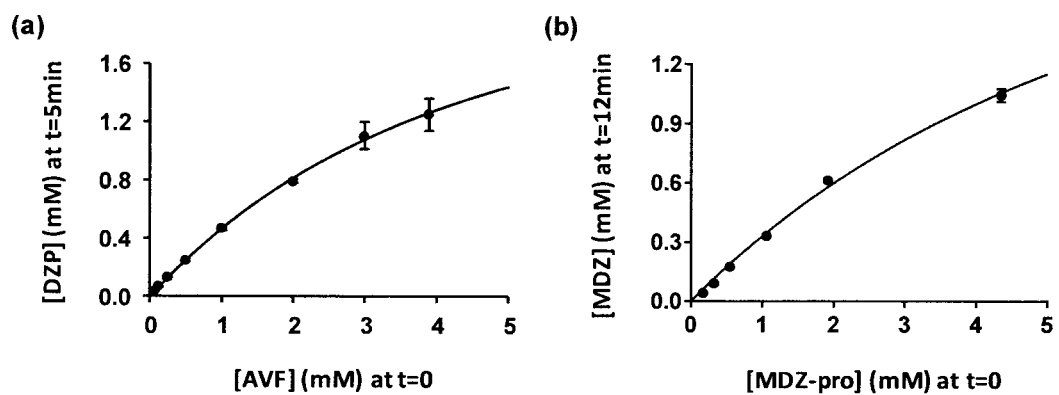
FIG. 4. Plots of degree of prodrug to drug conversion at fixed time, t, as a function of prodrug concentration, with fixed concentration of A.O. protease, pH=7.4, 32° C. Symbols represent experimental data±s.d. (n=3) and the solid line is the least squares fit to the integrated Michaelis-Menten equation. (a) Conversion of chirally pure avizafone ($AVF_p$) to DZP by 0.25 U/ml A.O. protease, at t=5 min. (b) MDZ-pro conversion to MDZ by 4.0 U/ml A.O. protease, at t=12 min.

The Michaelis Menten parameters for $AVF_p$ reactions were determined by carrying out reactions for t=5 min in solutions containing A.O. protease. Results, and fits to Eq. (1) for $AVF_p$ (at [E]=0.25 U/ml) are shown in FIG. 4a. For $AVF_p$, $K_M$=3.38±0.34 mM and $V_{max}$=0.518±0.030 mM/min. These values should replace those determined previously for $AVF_m$ (Kapoor M, et al., AAPS J, 2014, 16, 3, 577-585), since the enzyme is now established to mediate conversion of the S-enantiomer, exclusively.

Membrane Permeation Studies.

In separate experiments, solutions containing 900 µM $AVF_p$ or $AVF_m$ were rapidly mixed with A.O. protease (4 U/mL) in assay buffer (pH 7.4 at 32° C.), and administered at time zero on the apical side of MDCKII-wt monolayers cultured in a 12-well Transwell plate (Kapoor M, et al., AAPS J, 2014, 16, 3, 577-585; and Kapoor M, et al., Mol Pharm, 2013, 10, 9, 519-3524). The amounts of AVF and DZP permeating across the monolayer were then assayed over time. As shown in FIG. 3c, the rate and amount of DZP permeation was greater at each time point when AVF was chirally pure than when it was a mixture of enantiomers, as expected due to the incomplete and complete conversion of $AVF_m$ and $AVP_p$ to DZP, respectively. In the absence of enzyme, AVF (pure or mix) exhibited negligible permeation (data not shown).

MDZ-pro/Enzyme System

MDZ Equilibrium Solubility.

Equilibrium solubility of MDZ in assay buffer was determined at three temperatures: 25, 32 and 37° C. There was essentially no effect of temperature on drug thermodynamic solubility within this temperature range. Average MDZ solubility at pH 7.4 and 32° C. was 55±4 µM (15.5±1.2 µg/mL).

Enzyme Kinetics.

The extent of reaction was determined after t=12 min with MDZ-pro incubated, at different concentrations, in assay buffer with 4 U/ml A.O. protease. For conversion of MDZ-pro to MDZ, the following estimates (s.e.m.) were made using Eq. (1): $K_M$=5.86±0.83 mM and $V_{max}$=0.233±0.022 mM/min. The fit is shown in FIG. 4b. Complete mass balance was obtained at each time point and no drug precipitates were observed during the reaction.

Membrane Permeability of MDZ.

To assess transport of MDZ through the MDCKII-wt monolayer membrane, MDZ, 55 µM (S=1) was introduced on the apical side of the monolayer in a 12-well Transwell, and accumulation of MDZ on the basal side was assayed as a function of time. Results are given in FIG. 5a. Fitting the data to a two compartment model which takes the volumes of the apical and basal solutions into account, the clearance and permeability of the membrane were found, to be CL=0.11±0.01 mL/hr and permeability $P_{app}=2.65\times10^{-5}$ cm/s, respectively.

Conversion of MDZ-Pro and Permeation of MDZ.

Figure 5:
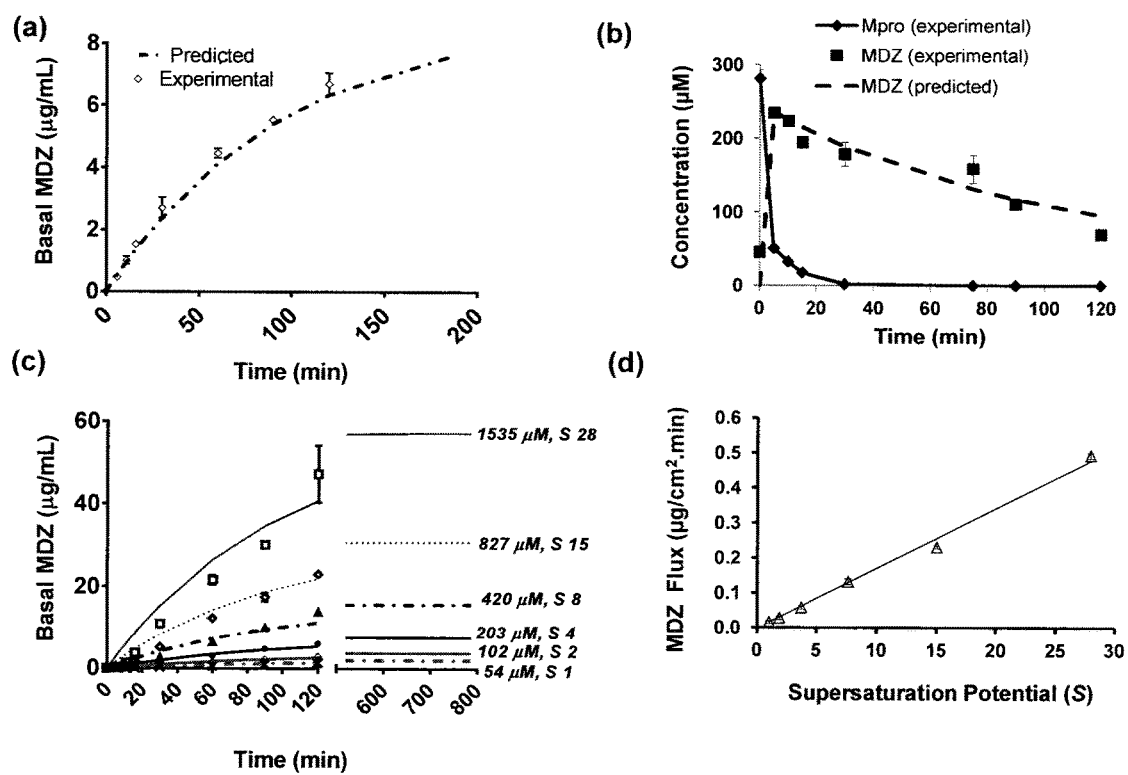
FIG. 5. (a) Permeation of MDZ across MDCKII-wt monolayer, following apical administration of saturated MDZ (55 μM, S=1). The dashed curve represents the data fitted to the following equation.

Rapidly mixed solutions of chirally pure MDZ-pro and A.O protease were administered onto the apical side of MDCKII-wt monolayers and MDZ-pro, and MDZ concentrations were analyzed on both the apical and basal sides as a function of time. An example of prodrug and drug kinetics in the apical compartment is shown in FIG. 5b (MDZ-pro 326 µM, A.O. protease 16 U/mL). Rapid conversion of prodrug (complete within 30 min) was followed by an extended residence of supersaturated drug in the apical chamber, with supersaturation reached in less than 5 min. After the experiment, microscopy was used to search for precipitates, but none were found. Apical concentrations of MDZ were close to those predicted, based on a two compartment model with input due to enzymatic conversion of MDZ-pro to MDZ, with assumed rate constant $k_{conv}=V_{max}/K_M$.

Accumulation of MDZ in the basal chamber following apical administration and conversion of MDZ-pro is plotted as a function of time in FIG. 5c. Again, data was well predicted by the two-compartment model. The basal MDZ concentrations approached predicted stationary values corresponding to equally supersaturated concentrations of MDZ on both the basal and apical sides. Initial fluxes of MDZ across the membrane, calculated using linear fits of basal accumulation at 5, 10, and 15 min, were linearly related to supersaturation potential as shown in FIG. 5d. Together, these results demonstrate that MDZ-pro can be administered at high supersaturation potential, and that the resulting MDZ remains supersaturated long enough to permeate completely through the monolayer without precipitation.

When MDZ-pro alone (without enzyme) was incubated with MDCKII-wt monolayers apically for 2 h, no prodrug or drug was detected in basal samples even at 2 mM initial prodrug concentration, indicating negligible prodrug permeation through MDCKII-wt monolayers and negligible conversion via endogenous enzymes.

Transepithelial electrical resistance (TEER) and Lucifer yellow permeability measurements were used to assess monolayer intactness following 2 h exposure to MDZ-pro, MDZ, A.O. protease (1-16 U/mL), MDZ-pro+enzyme, MDZ+enzyme and blank buffer solutions. % TEER values were unaffected by all treatments except for MDZ-pro/A.O. protease mixtures prepared at S≥15 (827 µM). The apparent toxic effects of MDZ-pro/enzyme at high MDZ concentrations may be due to the supersaturated MDZ product or the lysine that is produced when MDZ-pro is cleaved by the enzyme. It should be noted however that this effect, observed at high prodrug concentrations, did not alter the linearity of MDZ permeation, at least at early times (FIG. 5d). The two hour measurement time most greatly exceeds the likely exposure time of nasal tissue to any liquid formulation.

DISCUSSION AND CONCLUSION

We previously demonstrated rapid permeation of DZP produced from water soluble AVF/A.O. protease mixtures, administered in assay buffer pH 7.4, across MDCKII-wt membranes, an established model for nasal epithelium (Kapoor M, et al., AAPS J, 2014, 16, 3, 577-585). These mixtures produced supersaturated DZP solutions in situ without precipitation, leading to faster drug absorption compared to saturated DZP solutions. These aqueous prodrug/enzyme mixtures are hypothesized to have better patient tolerance compared to intranasal solutions prepared with organic co-solvents Hou H, Siegel R A, *J Pharm Sci*, 2006, 95, 4, 896-905).

A deficiency in our previous work was incomplete conversion of AVF to DZP. Upon further investigation, it was observed that AVF used as starting material, and unreacted AVF (remaining after AVF-A.O protease reaction), had different circular dichroism spectra, suggesting racemization during prodrug synthesis despite use of optically pure precursors. In the present work we implemented a different AVF synthesis scheme to prepare chirally pure prodrugs. Mosher's method confirmed that the newly synthesized prodrug was 99.0% chirally pure S-enantiomer, while the previously prepared $AVF_m$ was a mixture of enantiomers consisting of 77% S and 23% R. The new synthesis method therefore supersedes the old one. In this paper, we demonstrated complete conversion of the chirally pure S-AVF. The correlation between chiral purity and degree of conversion to DZP demonstrates that A.O protease acts stereospecifically on AVF.

Since MDZ is more potent than DZP in treating seizure emergencies, and more lipid soluble, we next applied our prodrug/enzyme strategy to MDZ. While AVF, given intramuscularly, has been available for decades as a battlefield anticonvulsant, MDZ-pro is a new molecule. Interestingly, MDZ-pro is also a substrate for A.O protease, and complete conversion of this chirally pure prodrug was observed.

The results of this and the previous work suggest that water-soluble prodrugs of poorly soluble benzodiazepines can be rapidly converted to supersaturated active drug, and that the drugs remain in their supersaturated state extended periods. Their absorption rates across mucosal membranes are proportional to their thermodynamic activities, which can greatly exceed those of saturated solutions. Supersaturated DZP and MDZ, generated enzymatically from prodrugs at the point of administration, may therefore be absorbed more rapidly than from other formulations that increase thermodynamic solubility, e.g. using organic solvents.

It should be noted that the residence time in the present experimental system is much longer than would be desirable for rapid nasal absorption of BZDs. However, we expect the nasal clearance in humans to be greater than that of the experimental monolayer system due to the extensive surface area of the nasal epithelium. This factor, by itself, would substantially reduce absorption time. The cellular permeability of the nasal epithelium to BZDs will also play a role in absorption rate. It is important to note that greater clearance across the nasal epithelium, due to its large surface area, will lead to rapid reduction in level of supersaturation. Thus, even higher doses of the prodrugs can presumably be administered without fear of precipitation.

In the present studies, the same enzyme, A.O. protease, was shown to catalyze conversion of both $AVP_p$ and MDZ-pro. There are two points worthy of mention. First, we noticed that the estimated $K_M$ values for the two prodrugs (3.38 mM for $AVF_p$ and 5.86 mM for MDZ-pro) are of comparable magnitude. However, much higher enzyme levels were required to produce comparable conversion rates for MDZ-pro compared to $AVF_p$. Calculating the catalytic efficiencies as $V_{max}$/(U/mL of A.O. protease), we obtain the values 2.07 mM/min/(U/ml) for $AVF_p$ and 0.0582 mM/min/(U/mL) for MDZ-pro. Second, since initiating the present studies, we became aware that the A.O. protease preparation is actually a combination of at least eight enzymes, each having its own pH and temperature profiles in cleaving a variety of substrates Inasmuch as the present results refer to a single pH and temperature for an enzyme mixture, future studies will be carried out to isolate and characterize the activity profiles of the enzyme fractions that are responsible for prodrug conversion.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A formulation suitable for nasal administration comprising: water, a prodrug of a therapeutic agent, and an enzyme that is suitable for intranasal conversion of the prodrug to the therapeutic agent, wherein the therapeutic agent is midazolam or a precursor of midazolam, and wherein the enzyme is a human aminopeptidase.

2. The formulation of claim 1, wherein the human aminopeptidase is EC 3.4.11.6.

* * * * *